United States Patent [19]

Fried et al.

[11] Patent Number: 4,690,925

[45] Date of Patent: Sep. 1, 1987

[54] (2-OXO-1,2,3,5-TETRAHYDROIMIDAZO-[2,1-B]QUINAZOLINYL) OXYALKYLAMIDES PROPERTIES HAVING PHOSPHODIESTERASE INHIBITING

[75] Inventors: John H. Fried, Palo Alto; Michael C. Venuti, San Francisco, both of Calif.

[73] Assignee: Syntex (U.S.A.) Inc., Palo Alto, Calif.

[21] Appl. No.: 734,633

[22] Filed: May 15, 1985

Related U.S. Application Data

[63] Continuation-in-part of Ser. No. 580,409, Feb. 15, 1984, abandoned.

[51] Int. Cl.[4] .................. A61K 31/505; C07D 487/04
[52] U.S. Cl. ..................................... 514/267; 544/250
[58] Field of Search .......................... 544/250; 514/267

[56] References Cited

U.S. PATENT DOCUMENTS

| Re. 31,617 | 6/1984 | Beverung, Jr. et al. | 544/250 |
|---|---|---|---|
| 3,932,407 | 1/1976 | Beverung, Jr. et al. | 544/250 |
| 3,983,119 | 9/1976 | Beverung, Jr. et al. | 544/250 |
| 3,983,120 | 9/1976 | Beverung, Jr. et al. | 544/250 X |
| 4,070,470 | 1/1978 | Nakagawa et al. | 544/128 X |
| 4,208,521 | 6/1980 | Crenshaw et al. | 544/250 |
| 4,256,748 | 3/1981 | Chodnekar et al. | 514/267 |
| 4,313,947 | 2/1982 | Nakagawa et al. | 514/234 |
| 4,490,371 | 12/1984 | Jones et al. | 544/250 X |
| 4,551,459 | 11/1985 | Jones et al. | 514/267 |
| 4,596,806 | 6/1986 | Ishikawa et al. | 514/267 |

FOREIGN PATENT DOCUMENTS

| 0000718 | 2/1979 | European Pat. Off. | |
| 0153152 | 8/1985 | European Pat. Off. | 514/267 |
| 2393795 | 1/1979 | France. | |
| 54-163825 | 12/1979 | Japan. | |
| 2001638 | 2/1979 | United Kingdom. | |

OTHER PUBLICATIONS

Lehninger, *Principles of Biochemistry*, Worth Publishers, Inc., (1982), p. 96.
Greenstein and Winitz, *Chemistry of the Amino Acids*, John Wiley and Sons, Inc., vol. 1, (1961), pp. 3-7.
Greenstein and Winitz, *Chemistry of the Amio Acids*, John Wiley and Sons, Inc., vol. 2, (1961), pp. 263-267.
European Journal of Medicinal Chemistry, 1982—17, No. 6, pp. 547-556, by Kienzle et al.
Journal of Pharmacology and Experimental Therapeutics, vol. 211, No. 1, (1979), pp. 26-30, Hidaka et al.
Kohga et al., Cancer Research, vol. 41, pp. 4710-4714, (11/81).
Pearlstein et al., Cancer Research, vol. 44, pp. 3884-3887, (09/84).

*Primary Examiner*—Donald G. Daus
*Assistant Examiner*—Diana G. Rivers
*Attorney, Agent, or Firm*—Liza K. Toth; Tom M. Moran

[57] ABSTRACT

Compounds according to the formula

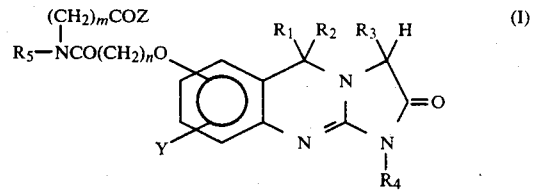

its optical isomers, or a pharmaceutically acceptable salt thereof wherein:

m and n are integers of 1 to 6;

$R_1$ is hydrogen or alkyl of 1 to 4 carbons;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbons, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_6$, halo, —NH$_2$, —N(R$_6$)$_2$, —NHCOR$_6$, —COOH, or —COO(R$_6$) group wherein R$_6$ is lower alkyl; phenyl or phenyl lower alkyl wherein phenyl is unsubstituted or substituted with 1 or more lower alkyl, halo or lower alkoxy groups or an —NH$_2$, —N(R$_6$)$_2$, —NHCOR$_6$, —COOH, or —COOR$_6$ group wherein R$_6$ is lower alkyl;

Y is hydrogen, alkyl of 1 to 4 carbon atoms, halo or lower alkoxy; and

Z is —OR$_7$ or —NR$_7$R$_8$ wherein R$_7$ and R$_8$ are independently hydrogen or lower alkyl.

21 Claims, No Drawings

(2-OXO-1,2,3,5-TETRAHYDROIMIDAZO-[2,1-B]QUINAZOLINYL) OXYALKYLAMIDES PROPERTIES HAVING PHOSPHODIESTERASE INHIBITING

This patent application is a continuation-in-part of U.S. Ser. No. 06/580,409, filed Feb. 15, 1984, and now abandoned.

BACKGROUND OF THE INVENTION

1. Field of the Invention

This invention relates to novel substituted 1,2,3,5-tetrahydroimidazo[2,1-b]quinazolines which possess phosphodiesterase inhibiting properties. More specifically the compounds of interest are (2-oxo-1,2,3,5-tetrahydroimidazo[2,1-b]quinazolinyl)-oxyalkylamides and their pharmaceutically acceptable salts.

2. Related Art

Publications of possible interest herein are: F. Kienzle, et al, *Eur. J. Med.*, 1982-17, No. 6d, pp 547–556 disclosing 1,5-dihydroimidazoquinazolinones as blood platelet aggregation inhibitors; Japanese patent No. 54-163825; and U.S. Pat. No. 3,932,407. These references are relevant primarily for their disclosure of similarly acting compounds, not because the compounds therein are structural analogues to the compounds herein.

SUMMARY OF THE INVENTION

In a first aspect this invention relates to compounds of the formula

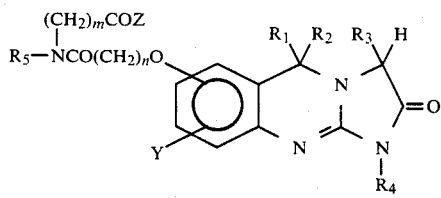

(I)

, its optical isomers, or a pharmaceutically acceptable salt thereof wherein:

$m$ and $n$ are integers of 1 to 6;

$R_1$ is hydrogen or alkyl of 1 to 4 carbons;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbons, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_6$, halo, —NH$_2$, —N(R$_6$)$_2$, —NHCOR$_6$, —COOH, or —COO(R$_6$) group wherein R$_6$ is lower alkyl; phenyl or phenyl lower alkyl wherein phenyl is unsubstituted or substituted with 1 or more lower alkyl, halo or lower alkoxy groups or an —NH$_2$, —N(R$_6$)$_2$, —NHCOR$_6$, —COOH, or —COOR$_6$ group wherein R$_6$ is lower alkyl;

Y is hydrogen, alkyl of 1 to 4 carbon atoms, halo or lower alkoxy; and

Z is —OR$_7$ or —NR$_7$R$_8$ wherein R$_7$ and R$_8$ are independently hydrogen or lower alkyl.

These compounds are 3',5'-cyclic AMP phosphodiesterase inhibitors useful as antithrombotic agents and the like in mammals.

Accordingly, a second aspect this invention relates to pharmaceutically acceptable compositions of one or more compounds according to Formula I wherein said compounds are combined with at least one pharmaceutically acceptable excipient.

Yet another aspect of this invention relates to a method for inhibiting 3',5'-cyclic AMP phosphodiesterase activity in a mammal, particularly, a human.

In yet another aspect, this invention relates to a method of treating heart failure by stimulating suppressed heart activity which occurs during heart failure.

Yet another aspect of this invention relates to a method for inhibiting platelet aggregation.

In yet a further aspect, this invention relates to a method of inhibiting tumor growth.

The above methods comprise administering a therapeutically effective amount of a compound of this invention alone or in admixture with a pharmaceutically acceptable excipient.

Yet another aspect of this invention relates to a process for making a compound of Formula I, which process comprises treating a compound of Formula II

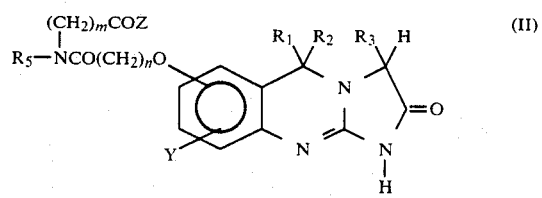

(II)

wherein m, n, $R_1$, $R_2$, $R_3$, $R_5$, Y and Z are as defined above, but wherein $R_5$, $R_7$ and $R_8$ are not hydrogen, with an N-alkylating agent, or treating a compound of Formula III

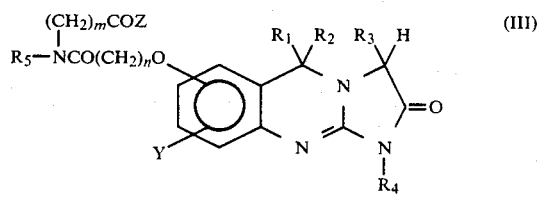

(III)

wherein m, n, $R_1$, $R_2$, $R_3$, $R_4$ and Y are as defined above and Z is —OR$_7$ wherein R$_7$ is lower alkyl, with base; or treating a compound of Formula IV

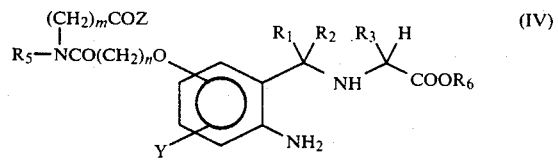

(IV)

wherein m, n, $R_1$, $R_2$, $R_3$, $R_5$, and Y are defined above, Z is —OR$_7$ wherein R$_7$ is lower alkyl or —NR$_7$R$_8$ wherein R$_7$ and R$_8$ are independently hydrogen or lower alkyl and $R_6$ is alkyl of 1 to 6 carbon atoms, serially with a halocyanogen and base; or treating a compound of the Formula V

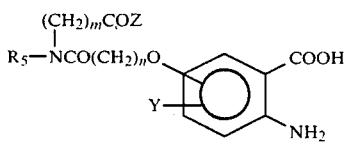

wherein m, n and Y are defined above and Z is $-OR_7$ wherein $R_7$ is lower alkyl or $-NR_7R_8$ wherein $R_7$ and $R_8$ are defined above, with 2-methylthiohydantoin to yield a compound of Formula (I) wherein $R_1$ and $R_2$ are an oxo group and $R_3$ and $R_4$ are both hydrogen; or converting the free acid of a compound of Formula I to a pharmaceutically acceptable salt; or converting a salt to the compound of Formula I to the corresponding free acid; or converting the free base of a compound of Formula I to a pharmaceutically acceptable acid addition salt; or converting a salt to the compound of Formula I to the corresponding free base; or converting a salt of the compound of Formula I to a corresponding pharmaceutically acceptable acid addition salt.

DETAILED DESCRIPTION OF THE PREFERRED EMBODIMENTS

Utility

These compounds are potent inhibitors of human platelet 3',5'-cyclic AMP phosphodiesterase activity. As a consequence, these compounds inhibit the ADP-induced aggregation of human platelets. Thus, these compounds are useful in the prevention or treatment of a variety of conditions related to platelet aggregation and thrombosis, for example, intravascular thrombosis, prevention of coronary thrombosis, prevention of transient ischemic episodes and prevention of platelet thrombosis and the prevention of thrombosis, thrombocytopenia or platelet activation associated with the use of prosthethic devices (artificial heart valves, etc.).

3',5'-Cyclic AMP is known to regulate the activity of numerous enzymes and mediates the action of several hormones. Studies have demonstrated that a deficiency in this cyclic AMP or an increase in the activity of a high affinity 3',5'-cylic AMP phosphodiesterase is associated with a variety of disease states. As inhibitors of 3',5'-cyclic AMP phosphodiesterase, compounds of this type are useful in the treatment or prevention of hypertension, asthma, diabetes, obesity, immune dysfunctions, psoriasis, inflammation, cardiovascular disease, tumor metastasis, cancer and hyperthyroidism. A more complete description of the various prophylactic and therapeutic activities of cyclic AMP phosphodiesterase inhibiting compounds can be found in the following references: Amer, S. M., "Cyclic Nucleotides As Targets For Drug Design," *Advances in Drug Research*, Vol. 12, 1977, Academic Press, London, pp 1–38; Weinryh, I. et al, *J. Pharm. Sci., pp* 1556–1567, (1972); Amer, S. M. & W. E. Kreighbaum, *J. Pharm. Sci.*, V 64, pp 1–37, (1975); and Harris, D. N., et al, *Enzyme Inhibitors As Drugs*, McMillan & Co., Ed-M. Sandler, pp 127–146, (1980).

The compounds of the present invention also have inotropic activity. They can strengthen myocardial contraction force by which the heart ventricles can pump the blood into the periphery. Consequently, these compounds also are useful in treating myocardial failure.

Furthermore, the compounds of the present invention also have anti-metastatic activity.

Definitions

The compounds of the present invention are numbered as follows:

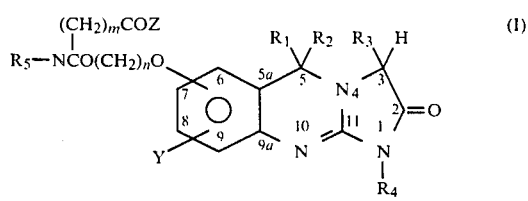

For the purpose of this disclosure, the compounds of the present invention are represented as having the single structural formulation represented by Formula I. However, when $R_4$ is hydrogen, compounds of Formula I can exist in several possible tautomeric forms established by the following core structures:

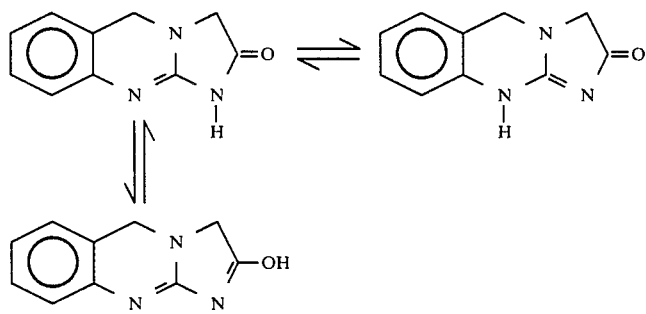

All tautomers are part of the present invention.

The compounds of this invention may be prepared as structural isomers wherein the oxyalkylamide side chain is substituted on the benzene ring at any of the four different available positions. This fact is graphically represented in the generic formula by the drawing of the line into the benzene ring without it being directed to a particular carbon. In addition, the Y substituent or substituents may be present at any of one or more of the remaining ring positions as indicated by Formula I.

Also within the scope of this invention are the optical isomers of those compounds having an asymmetric center, such as when positions 3 and/or 4 of the 1,2,3,5-tetrahydroimidazo[2,1-b]quinazolin-2-one structure are substituted with a substituent other than hydrogen. In addition $R_5$ may have an asymmetric center.

Accordingly, the compounds of the present invention may be prepared either in optically active form or as racemic mixtures. Unless otherwise specified, where appropriate, products of the various synthetic steps described herein will be a racemic mixture. However, the scope of the subject invention herein is not limited to the racemic mixture, but is to encompass the separated individual optical isomers of the disclosed compounds.

If desired, the compounds herein may be resolved into their optical antipodes by conventional resolution means, for example, by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-α-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers.

For the purpose of this invention, the following phrases should be understood to have the recited meaning.

When reference is made to "alkyl of 1 to 6 carbon atoms" it is meant that there is a branched or unbranched saturated hydrocarbon chain containing, in total, that number of carbon atoms. The phrase refers specifically to such substituents as, for example, methyl, ethyl, n-propyl, i-propyl, n-butyl, tert-butyl, n-pentyl, n-hexyl and the like. The terms "alkyl of 1 to 4 carbon atoms" and "lower alkyl" are used interchangeably and mean methyl, ethyl, n-propyl, i-propyl, n-butyl, t-butyl, and the like. The term "alkyl" or the prefix "alk" (as in "alkoxy"), when not inconsistently qualified (e.g., by the term "lower"), means a branched or unbranched saturated hydrocarbon chain containing from 1 to 12 carbon atoms.

"Lower alkoxy" means the group —OR wherein R is lower alkyl as defined in the foregoing paragraph.

When it is recited that $R_1$ and $R_2$ can be combined to form an oxo group, it is meant that at position 5, as numbered above, the carbon has a double bond to an oxygen atom.

In the instance where the $R_3$ group is substituted with a hydroxyalkyl substituent, that hydroxy function can be converted to an ester by reaction with a carboxylic acid. Such an acid may be any unbranched or branched aliphatic acid having 1 to 6 carbon atoms such as, for example, formic acid, acetic acid, propionic acid, butyric acid, pentanoic acid, hexanoic acid or an isomer of these acids which has up to 6 carbon atoms and is fully saturated. These esters are referred to herein as "aliphatic acylates of 1 to 6 carbon atoms." In addition, the carboxylic acid may be an aryl acid, exemplified by benzoic acid and having up to 7 to 12 carbon atoms. Representative radicals are, in addition to benzoic acid, phenylacetic acid, 3-phenylpropionic acid, 4-phenylbutyric acid, 6-phenylhexanoic acid and the like. Such acids serve to define and exemplify the term directed to the ester product of the reaction, "aryl acylates of 7 to 12 carbon atoms."

The term, "α-amino acid side chains," is meant to include naturally occurring amino acid side chains, commercially available synthetic amino acid side chains, and amino side chains which can be synthesized by one of ordinary skill in the art of organic chemistry; where in each instance the amino group and the side chain are both attached to the α-carbon.

The phrase "unsubstituted or substituted" is used herein in conjunction with cycloalkyl and aryl substituents to indicate the ring may have on it only hydrogen or, alternatively, may be substituted with one or more of the enumerated radicals as specifically indicated.

"Cycloalkyl of 3 to 8 carbon atoms" refers to a saturated aliphatic ring which contains 3 to 8 carbon atoms and which is substituted directly onto the nitrogen without any intervening methylene groups. Such radicals are, for example, cyclopropyl, cyclobutyl, cyclopentyl, cyclohexyl, cycloheptyl and cyclooctyl.

When reference is made to "cycloalkyl lower alkyl of 4 to 12 carbon atoms," is it meant that the substituents denoted as cycloalkyl of 3 to 8 carbon atoms in the preceding paragraph are attached to the nitrogen (to which $R_5$ is attached) by means of a saturated branched or unbranched carbon chain which may have 1 to 4 carbon atoms. Such substituents are, for example, cyclobutylmethyl, 4-cyclobutylbutyl, cyclopentylmethyl, 4-cyclopentylbutyl, cyclohexylmethyl, 4-cyclohexylbutyl, cycloheptylmethyl and 4-cycloheptylbutyl, to name a few examples.

In addition, the cycloalkyl or cycloalkyl lower alkyl radicals recited in the two foregoing paragraphs may be substituted with a radical chosen from the group consisting of lower alkyl, lower alkoxy, —OH, —OCOR$_6$, halo, —NH$_2$, —N(R$_6$)$_2$, —NHCOR$_6$, —COOH, and —COO(R$_6$) wherein R$_6$ is lower alkyl.

"Phenyl lower alkyl" means a group having at least one and up to four methylene groups with an ω-phenyl group. In this instance the carbon chain is linear, not branched. The phenyl group may be unsubstituted, i.e., contain only hydrogen, or it may be substituted with up to 5 substituents of a single functionality or a combination of the several recited substituents. Examples of unsubstituted phenyl lower alkyl are benzyl, phenylethyl, phenylpropyl and phenylbutyl. Examples of substituted phenyl lower alkyl are 4-halophenylalkyl, 2,4-dihalophenylalkyl, 2,4,6-trihalophenylalkyl or 2,3,4,5,6-pentahalo-phenylalkyl wherein halo is as defined below.

In addition, the phenyl group may be substituted with one or more lower alkyl groups such as methyl, ethyl, propyl, or the like. One or more lower alkoxy groups may also be substituted on the phenyl ring. Also, phenyl may be substituted with a radical chosen from the group consisting of —NH$_2$, —N(R$_6$)$_2$, —NHCOR$_6$, —COOH, and —COOR'$_6$ group wherein R$_6$ is lower alkyl.

The term "halo" refers to fluoro, chloro and bromo and iodo.

The prefix D- and L- are used to describe the individual optical isomers having an asymmetric center at the 3 or 5 position in the 1,2,3,5-tetrahydroimidazo[2,1-b]quinazolin-2-one structure.

Perhexylenyl refers to the substituent dicyclohexyl-2-(2-piperidyl)ethane which is disclosed in British Patent No. 1,025,578.

"Pharmaceutically acceptable salt" refers to those salts which retain the biological properties and efficacy of the free acid or base and which are not biologically or otherwise undesirable, formed with inorganic or organic acids or bases. Inorganic acids which may be used are, for example, hydrochloric acid, hydrobromic acid, sulfuric acid, nitric acid, phosphoric acid and the like. Exemplary organic acids are acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

The compounds of Formula I in free base form may be converted to the acid addition salts by treating the base with a stoichiometric excess of the appropriate organic or inorganic acid. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

Administration and Dosage

Administration of the active compounds and salts thereof described herein can be via any of the accepted modes of administration for agents which are cyclic AMP phosphodiesterase inhibitors. These methods include oral, parenteral and otherwise systemic or aerosol forms.

Depending on the intended mode of administration, the compositions used may be in the form of solid, semisolid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain from about 1% to about 99% active ingredient, preferably about 10% to about 50%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. Nos. 3,710,795 and 3,773,919.

For systemic administration via suppository, traditional binders and carriers include, e.g. polyalkylene glycols or triglycerides. Such suppositories may be formed from mixtures containing active ingredient in the range of from about 0.5% to about 10% and preferably from about 1% to about 2%.

The amount of active compound administered will of course, be dependent on the subject being treated, the type and severity of the affliction, the manner of administration and the judgment of the prescribing physician. In any case, a therapeutically effective amount of the drug either alone or in combination with the various excipients listed above or otherwise known will be administered. For the purpose of this invention, a therapeutically effective amount is in the range of from about 1 to about 25 mg/kg of body weight, and preferably from about 5 to about 10 mg/kg.

Preferred Embodiments

Preferred embodiments of the present invention are those compounds wherein m is 1 or 2, n is 3 or 4; $R_1$, $R_2$ and $R_3$ are hydrogen and $R_4$ is hydrogen or methyl; or compounds wherein m is 1 or 2, n is 3 or 4, $R_1$, $R_2$ and $R_4$ are hydrogen, $R_3$ is alkyl of 1 to 6 carbon atoms, phenyl, benzyl, hydroxy lower alkyl and its aliphatic acylates of 1 to 6 carbon atoms or aryl acylates of 7 to 12 carbon atoms, or carbamoyl alkyl and their optical isomers.

More preferred embodiments are those compounds wherein m is 1; n is 3 or 4; $R_1$, $R_2$ and $R_3$ are hydrogen; $R_4$ is hydrogen or methyl, and $R_5$ is alkyl of 1 to 6 carbon atoms, cycloalkyl of 3 to 8 carbon atoms, cycloalkyl lower alkyl of 4 to 12 carbon atoms, phenyl or phenyl lower alkyl unsubstituted or substituted with 1 or more lower alkyl, halo or lower alkoxy groups; Y is hydrogen and Z is —OH or —NH$_2$.

Most preferred are those compounds wherein m is 1 or 2, n is 3 or 4, $R_1$, $R_2$, $R_3$ and $R_4$ are hydrogen, and $R_5$ is alkyl of 1 to 6 carbon atoms or cycloalkyl of 3 to 8 carbon atoms; Y is hydrogen and Z is —OR wherein R is hydrogen or lower alkyl or —NH$_2$.

PREPARATION AND EXAMPLES

Compounds of the present invention can be made by several methods. In this disclosure, the process for preparing the claimed compounds begins with a hydroxy-2-nitrobenzaldehyde which is reacted with an ω-haloalkylester which serves to introduce the alkyl side chain onto the benzene ring. The ester is then hydrolyzed, converted to the acid chloride and treated with the appropriate secondary ω-amino acid ester or amide. If $R_1$ is to be a group other than hydrogen, that group is introduced into the compound at this point by treating the amide with an appropriate Grignard reagent, which reacts with the aldehyde function, and then oxidizing the resulting alcohol to the ketone. The aldehyde or ketone-containing amide is then treated with an α-amino acid or a salt thereof followed by a cyclization step employing a halo cyanogen and base. Acid addition salts, etc are prepared from this base as needed or desired.

Compounds of the present invention are prepared by the reaction sequence outlined in the following Reaction Schemes. Z is —OR$_7$ wherein lower alkyl or —NR$_7$R$_8$ as defined above.

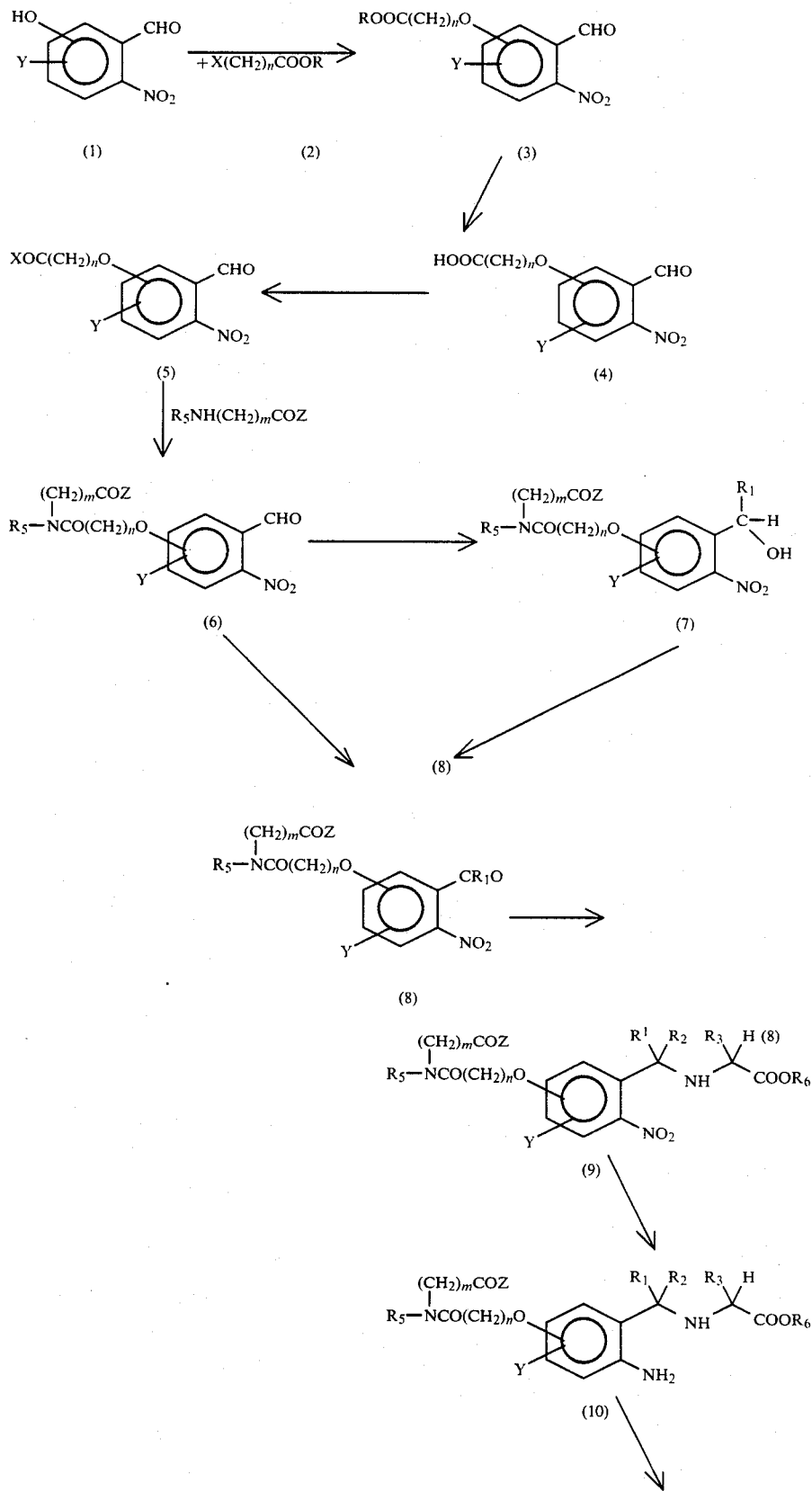

-continued
REACTION SCHEME A

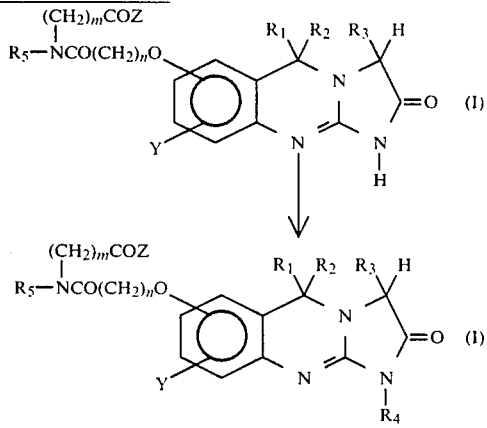

In Reaction Scheme A, the phenols of Formula (1) are known in the art and a number of them are readily available from commercial sources such as Aldrich Chemical Co., Milwaukee, Wis. They are converted to the ω-(formylnitrophenyl)oxyalkyl esters by treating the phenol with an ω-halo substituted alkyl ester of Formula (2). Generally, the reaction is carried out by mixing a mole equivalent of ω-haloalkylester, or up to a 20% excess thereof, with the parent phenol compound in a dry, dipolar aprotic solvent under an inert atmosphere. Solvents which may be used in this reaction are, for example dimethylformamide, propylene carbonate, ethylene carbonate, diethylcarbonate, dimethylcarbonate, tetrahydrofuran and the like. Dimethylformamide is preferred. Preferably the reaction will be carried out in a predried solvent and will be blanketed under a dry inert atmosphere such as nitrogen.

A molar amount, but up to a 30% excess, of weak base is added to the solution to effect the reaction. This weak base may be, for example, an alkali metal carbonate or the like, preferably potassium carbonate. The reaction requires between about 0.25 and about 2 hours at between about room temperature and about 200° C. Preferably the reaction will be carried out for about 1 hour at about 100° C.

Reaction products are isolated by conventionally known methodologies, preferably by solvent extraction into a compatible organic solvent. The Formula (3) product may be further purified by distillation or other appropriate means.

Conversion of the ester to its corresponding acid involves saponification using well known conditions and reagents. For example, a dilute solution of a strong base, such as an alkali metal base, is added to an alcoholic solution of the ester in small portions and the reaction is allowed to run for about 10 to about 60 minutes at a temperature between about 0° and about 50° C. Alcohols which may be used as the solvent for this reaction are, for example, methanol, ethanol, propanol and isopropanol or the like, though it is preferable to use ethanol. The base may be, for example, sodium hydroxide, potassium hydroxide, or lithium hydroxide and the like, but it is preferable and most convenient to use sodium hydroxide. While the concentration of the added base may range between 1 and 6N it is preferable to begin with a 3N solution and add it to the reaction mixture in a ratio of 1 part base for every 4 parts of alcohol solution. Preferably the reaction is allowed to run for about 30 minutes at room temperature after which the solution is neutralized with a concentrated solution of a strong acid such as hydrochloric acid or the like and the solvent evaporated. The product is then further isolated by organic solvent extraction. Crystallization from an appropriate organic solvent gives Formula (4) type compounds.

The conversion of Formula (4) acids to the acid chloride of Formula (5) is a known reaction. The reaction is carried out in a stirred solution of acid in a non-polar, non-reactive solvent such as benzene or toluene or the like to which has been added a small amount of a dipolar aprotic solvent such as dimethylformamide or the like by the addition of an acid halide forming agent, preferably an acid chloride forming agent such as oxalyl chloride. The acid chloride forming reagent should be present in about a 25 to 75% molar excess, preferably a 50% excess, in order to effect a stoichiometric conversion of the acid to the acid halide.

The reaction is allowed to proceed at a temperature between about 0° and about 45° C. for a time between about 15 minutes and about 2 hours. Preferable reaction conditions are about 20° C. for about 1 hour by which time the suspended acid should be completely dissolved.

Without further isolation, the solvent in which the acid chloride is dissolved is converted to a polar solvent by repetitive evaporation and dissolution of the acid chloride in the new polar solvent. This polar solvent may be, for example, an ether such as tetrahydrofuran or diethylether, preferably tetrahydrofuran and preferably dry.

Preparation of the amide from the acid chloride is effected by means of the catalyst 4-dimethylaminopyridine (DMAP) under anhydrous conditions and an inert atmosphere. The acid chloride is dissolved in a dipolar aprotic solvent, such as tetrahydrofuran, and added to a solution of the secondary ω-amino acid ester or amide which has been dissolved in a dipolar aprotic solvent containing an organic base, for example a trialkylamine, or the like but preferably triethylamine. The ester or amide will be present in a slight molar excess relative to the acid chloride. The DMAP catalyst is present in the mixture in an amount up to a 10% molar amount relative to the acid chloride. During addition of the acid chloride, the reaction mixture is maintained at a temperature of between about −10° to about +10° C. The inert atmosphere is preferably provided by the use of dry nitrogen.

The secondary ω-amino acid esters or amides are prepared by the general procedure of Speziale, A. J., E. G. Jaworski, *J. Org. Chem.*, 25, 728 (1960).

When addition of the acid chloride is complete the solution is warmed to between about 15° and about 35° C., preferably to room temperature, and the reaction is allowed to proceed at that temperature for between about 30 minutes and about 4 hours, preferably about 2 hours.

When $R_1$ is alkyl or phenyl, that moiety may be introduced into the compound by reacting the Formula (6) aldehyde with a Grignard reagent or an alkyl lithium compound and then oxidizing the resulting secondary alcohol to the ketone represented by Formula (8).

Alkyl magnesium halide reagents are readily available or may be easily prepared from the alkyl halide and magnesium, a process well-known in the synthetic arts. Formation of the alcohol is effected by adding the aldehyde to a cooled ethereal solution of Grignard reagent wherein the Grignard reagent is present in a 10% molar excess relative to the aldehyde. After addition of the aldehyde is complete, the reaction is refluxed for about 1 to about 4 hours, preferably about 2 hours. Degradation of the magnesium halide derivative to obtain the alcohol is carried out by dropwise addition of a mineral acid, for example a 25% sulfuric acid solution. This solution is neutralized with a weak base and the alcohol isolated in preparation for treatment with an oxidizing agent to regenerate the oxo group.

The oxidation of Formula (7) type compounds is carried out via some strong oxidizing agent under selected conditions which minimize amide oxidation. There may be used, for example, a chromium trioxide-pyridine complex or the like. Preferably the reaction will be carried out under anhydrous conditions under an inert atmosphere and in a polar organic solvent which is inert to the oxidizing reagent, such as a halogenated hydrocarbon. Reaction temperatures will between about 0° to about 100° C. for a period of about 1 to about 8 hours. A 10% molar excess of oxidizing agent relative to the alcohol is sufficient to effect the desired oxidation.

Herein a preferred oxidizing reagent is the Collins reagent [J. C. Collins, et al., Tetrahedron Letters, p 3363 (1968)] which employs a chromium trioxide-pyridine complex in a halogenated hydrocarbon solvent system. The reaction is carried out under anhydrous conditions in an inert atmosphere. The preferred organic solvents are for example, methylene chloride, carbon tetrachloride, ethylene chloride, or the like. The inert atmosphere is maintained by the use of a dry inert gas, preferably dry nitrogen. Usually a temperature between about 0° to about 50° C. for a period of about 0.5 to about 5 hours is generally sufficient to effect the reaction. Most preferably the reaction will be carried out in dry methylene chloride under a dry nitrogen atmosphere for about 1 hour at room temperature.

Formula (6) and Formula (8) compounds may then be converted to compounds of Formula (9) by reacting the aldehyde or ketone with an α-amino acid ester. For the purposes of this invention any lower alkyl ester of a naturally occurring α-amino acids or any synthetic α-amino acid ester may be used in the practice of this invention. Generally, the reaction is carried out at a temperature between about 0°–50° C., preferably ambient temperature. A time of between 1 to 8 hours is sufficient to effect the reaction though 3–4 hours is preferable. The reaction is generally carried out in a polar solvent such as an alcohol, for example, methanol, ethanol, propanol, or the like in which the aldehyde/ketone and the ester are soluble. It is preferable to add a water-scavenging agent such as molecular sieves in order to remove water generated during the reaction process.

Initially, a reaction mixture is prepared which contains the carbonyl compound (aldehyde (6) or ketone (8)), about a two-fold molar amount of the α-amino acid ester as an acid addition salt, and the water scavenging agent. To this mixture is added a large molar excess of the α-aminocarboxylic acid ester, about 6–10 fold excess. The solution is generally maintained between about 10° to about 30° C. during this addition process. After addition of the ester is complete, there is added a cyanoborohydride reducing agent in a molar amount of about one-half that of the carbonyl compound. The reaction is allowed to proceed at a temperature between about 10° to about 30° C., preferably at room temperature for a period of between about 1 to about 6 hours, most preferably about 3 to about 4 hours.

While the reaction product may be isolated for characterization, etc., that is not necessary. It is most convenient to simply remove precipitated solids, i.e, the molecular sieves and borate salts, by filtration, evaporate the solvent and to take up the residue in an organic solvent. This solution may then be washed with a base and brine to remove impurities, after which the solvent is removed and the resulting residue used directly in the next reaction step.

Reduction of the nitro group is most conveniently carried out by catalytic hydrogenation. This reaction may be accomplished by conventionally known means. As practiced herein, the residue from the previous reaction step is dissolved in an appropriate solvent such as, for example, a simple alcohol such as methanol or ethanol. A transition metal catalyst which will selectively reduce the nitro group to the amine without affecting the amide or the phenyl ring is preferred. A preferred catalyst is a palladium catalyst and most preferably it will be palladium on carbon such as the readily available 10% palladium/carbon catalyst.

A small amount of the palladium/carbon catalyst, i.e., between about 0.5 and about 1.5 grams, will generally be sufficient to effect the reduction. The alcoholic reaction mixture is placed under hydrogen at room temperature and allowed to proceed until an equivalent of hydrogen has been taken up. Isolation by the hydrogenation product is readily accomplished by filtration to remove the catalyst after which the reaction product may be used directly in the following step.

Cyclization of the amine (10) to give (I), wherein $R_4$ is hydrogen, is achieved by means of a cyanogen halide, preferably the bromide. A 5 to 10% molar excess of cyanogen halide is added to the solution from the previous reaction. The resulting solution is refluxed overnight, preferably about 16 hours.

The resulting reaction mixture is then treated with a solution of a strong base for about 0.5 to about 4 hours at a temperature between about 0° and about 50° C. Bases which may be used to effect this reaction are alkali metal bases, such as sodium hydroxide, ammonium hydroxide, potassium hydroxide and the like. They are used at a concentration of between about 1 to 6N, preferably 2N. A molar amount of base equivalent to that of the cyanogen halide employed in the previous step is employed in this final reaction step. Preferably the reaction will be allowed to proceed for about 2 hours at room temperature during which time the product generally will precipitate as a powder. The product, Formula I wherein $R_4$ is hydrogen, can be further isolated and characterized by filtration or centrifugation, followed by drying or by recrystallization from an appropriate organic solvent.

Further transformation of compounds wherein $R_4$ is H to those where $R_4$ is alkyl, benzyl, etc., is accomplished by treating the former with alkylating agents and a strong base, such as potassium tert-butoxide or sodium hydride in a dipolar aprotic solvent such as dimethyl formamide.

The optical isomers of Formula (I) wherein $R_3$ is a substituent other than hydrogen can be prepared following the same procedures as described above except while reacting with the carbonyl compound (6) or (8), an optically active α-aminocarboxylic acid ester ($NH_2CHR_3COOR_6$) should be used.

The compounds of Formula I in free base form may be converted to the acid addition salts by treatment with a stoichiometric excess of the appropriate organic or inorganic acid. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

The acid addition salts of the compounds of Formula I may be decomposed to the corresponding free base by treatment with a stoichiometric excess of a suitable base, such as potassium carbonate or sodium hydroxide, typically in the presence of aqueous solvent, and at a temperature of between about 0° C. and about 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower $pK_a$ than the acid component of the starting salt. This conversion is carried out at a temperature between about 0° C. and the boiling point of the solvent.

An alternative route for preparing the compounds of Formula (I), wherein $R_1$ and $R_2$ are combined to form an oxo group and $R_3$ and $R_4$ are hydrogen is exemplified by the following reaction scheme.

REACTION SCHEME B

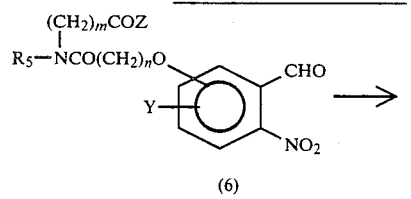

(6)

-continued
REACTION SCHEME B

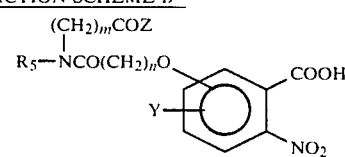

(11)

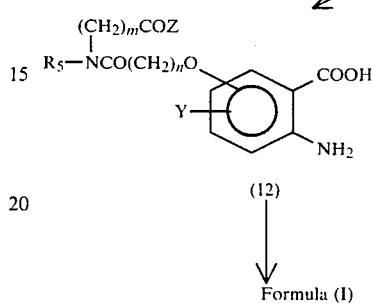

(12)

↓

Formula (I)

The compounds of Formula (6) are prepared as described above in Reaction Scheme A.

The compounds of Formula (11) are prepared by oxidizing the corresponding aldehydes with an oxidizing agent such as silver acetate, sodium chlorite-sulfamic acid, chromium trioxide-pyridine complexes or alkylammonium permanganates, for example. Usually the reaction will be carried out under an inert atmosphere in a dry, nitrogen-containing solvent at a temperature between about 0° and about 50° C. for a period of about 15 minutes to about 3 hours. Preferably the oxidation will be effected by an alkylammonium permanganate such as tetra-butylammonium permanganate in dry pyridine under a dry nitrogen blanket. The reaction is complete in about 1 hour at room temperature.

Reduction of the nitro group to obtain the anthranilic acid compounds of Formula (12) is by catalytic hydrogenation. This reaction employs a heavy metal catalyst dispersed in a simple alcohol containing the nitroacid and put under hydrogen at room temperature until hydrogen uptake is complete. In this instance, it is preferable to add 10% palladium-on-carbon to an ethanolic solution of the nitroacid and place the mixture under about 60 psi hydrogen overnight. Alternatively, the hydrogenation can be carried out with the addition of a mineral acid such as hydrogen chloride, which procedure gives the acid salt directly as a hygroscopic solid.

The amines of Formula (12) are converted directly to Formula I compounds by treating the acids, dissolved in a simple alcohol, with a 2-3 molar excess of 2-methylthiohydantoin. Generally the reaction is carried out under reflux for about 1 to about 6 hours. Preferably the reaction will be carried out in ethanol under reflux for about 3 hours.

REACTION SCHEME C

Compounds of Formula I may also be prepared from the 7-hydroxy-1,2,3,5-tetrahydroimidazo[2,1-b]quinazolin-2-one or its 6, 8 or 9-hydroxy analogues by the sequence of steps set out below.

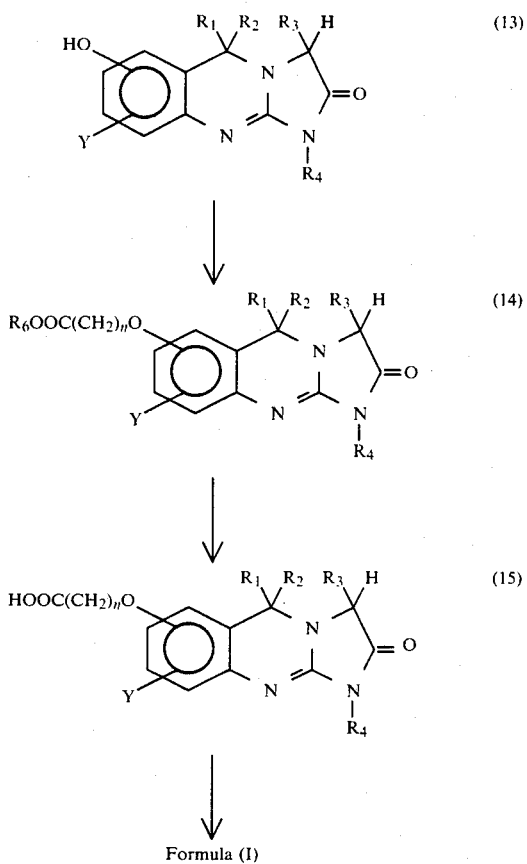

Formula (I)

The compounds of Formula 13 are prepared as described in U.S. Pat. No. 3,932,407 which is incorporated herein by reference.

Alkylation of the hydroxy compounds is achieved by the use of ω-bromoalkanoates (10% molar excess) in a dipolar solvent such as dimethylformamide in the same manner described for the preparation of Formula 3 compounds in reaction Scheme A. Ester hydrolysis, to give Formula 14 compounds, is carried out in the same manner as described hereinabove for the conversion of Formula 3 compounds to those of Formula 4 in reaction Scheme A.

Amides are prepared directly from the acid by condensation means. The reaction of the acid and an amide-forming agent may be carried out in a dipolar aprotic solvent such as dimethylformamide at a temperature between about 0° and about 40° C. For example, first the acid and a 10% molar excess of 1-hydroxybenzotriazole is dissolved in the reaction medium, after which a dialkylcarbodiimide, preferably diisopropylcarbodiimide, is added. After a period of about 0.25 to about 2 hours, preferably about 1 hour, a solution of methyl N-cyclohexyl glycinate or a like compound (20% molar excess) and N-methyl morpholine (20% molar excess) is added. Overnight stirring at about ambient temperature completes the reaction.

The following preparations and examples are set out to illustrate the reaction steps graphically recited above.

PREPARATION 1

Methyl N-cyclohexylglycinate

A solution of cyclohexylamine (34.3 ml) and diazobicycloundecene (DBU, 44.8 ml) in dry tetrahydrofuran (500 ml) under a nitrogen atmosphere was cooled to 0° C. and was treated dropwise with a solution of methyl bromoacetate (28.4 ml) in tetrahydrofuran (50 ml). After stirring at room temperature overnight, the mixture was filtered to remove precipitated DBU-hydrobromide and the solvent evaporated. The resulting residue was dissolved in ether (200 ml), washed with water (2×100 ml), and brine (2×100 ml). The organic extract was dried, filtered and evaporated. Fractional distillation provided 21.1 g., b.p. 160°–170° C. (0.2 mm).

PREPARATION 2

N-Cyclohexyl Glycinamide

A solution of methyl N-cyclohexyl glycinate (10 g) in methanol (50 ml) was saturated with ammonia and heated overnight at 80° C. in a pressure apparatus. The reactor was cooled and the solvent evaporated to give the solid amine, N-cyclohexyl glycinamide, m.p. 112°–113° C. Similarly, treatment of methyl N-cyclohexyl glycinate with other amines of the formula $R_7R_8NH$ will give the corresponding cyclohexyl $R_7R_8NH$ N-substituted acetamides (for Example 1).

PREPARATION 3

The preparation of ω-((formyl-nitrophenyl)oxy)alkyl acid esters, Formula 3, are described herein.

To a solution of 5-hydroxy-2-nitrobenzaldehyde (84.0 g) and ethyl 4bromobutyrate (86 ml) in dry dimethylformamide (500 ml) blanketed under dry nitrogen was added potassium carbonate (76.0 g). The reaction mixture was heated to 100° C. for 1 hour. This mixture was cooled, and the solvent removed by evaporation to give a dark brown syrup. This residue was partitioned between ethyl acetate and saturated sodium carbonate (500 ml each). The organic layer was washed with additional saturated sodium carbonate (3×500 ml), and with brine (2×500 ml), dried, filtered and evaporated to give a dark brown syrup. Kugelrohr distillation (180° C., 0.2 mm) afforded ethyl 4-((3-formyl-4-nitrophenyl)oxy)butyrate (95 g) as a bright yellow syrup which slowly darkened upon standing.

Using the above procedure, but substituting the appropriate aldehyde for 5-hydroxy-2-nitrobenzaldehyde and alkyl ω-bromoalkanoates for ethyl 4-bromobutyrate there may be prepared, for example, the following compounds:

ethyl 4-(2-chloro-3-formyl-4-nitrophenyl)oxybutyrate;
ethyl 4-(3-formyl-4-nitro-5-chlorophenyl)oxybutyrate;
ethyl 4-(2-chloro-4-nitro-5-formylphenyl)oxybutyrate;
ethyl 4-(3-formyl-4-nitro-5-fluorophenyl)oxybutyrate;
ethyl 4-(2-fluoro-3-formyl-4-nitrophenyl)oxybutyrate;
ethyl 4-(2-methyl-3-formyl-4-nitrophenyl)oxybutyrate;
ethyl 4-(2-formyl-3-nitro-6-fluorophenyl)oxybutyrate;
ethyl 4-(2-formyl-3-nitro-4-chlorophenyl)oxybutyrate;
ethyl 4-(2-formyl-3-nitro-5-fluorophenyl)oxybutyrate;
ethyl 4-(2-formyl-3-nitrophenyl)oxybutyrate;
ethyl 4-(2-formyl-3-nitro-5-methylphenyl)oxybutyrate;
ethyl 4-(2-formyl-3-nitro-6-fluorophenyl)oxybutyrate;
ethyl 4-(2-nitro-3-formylphenyl)oxybutyrate;
ethyl 4-(2-nitro-3-formyl-5-methylphenyl)oxybutyrate;
ethyl 4-(3-nitro-4-formyl-6-fluorophenyl)oxybutyrate;
ethyl 4-(2-chloro-4-formyl-5-nitrophenyl)oxybutyrate;
ethyl 4-(3-nitro-4-formylphenyl)oxybutyrate;
ethyl 4-(3-nitro-4-formyl-5-methylphenyl)oxybutyrate;
ethyl 4-(2-nitro-3-formyl-6-fluorophenyl)oxybutyrate;

ethyl 4-(2-nitro-3-formyl-6-chlorophenyl)oxybutyrate;
ethyl 7-(3-formyl-4-nitrophenyl)oxyheptanoate;
ethyl 7-(2-chloro-3-formyl-4-nitrophenyl)heptanoate;
ethyl 7-(2-methyl-3-formyl-4-nitrophenyl)heptanoate;
ethyl 7-(3-formyl-4-nitro-5-chlorophenyl)heptanoate;
ethyl 7-(2-formyl-3-nitrophenyl)heptanoate;
ethyl 7-(2-formyl-3-nitro-4-fluorophenyl)heptanoate;
ethyl 7-(2-methyl-3-formyl-4-nitrophenyl)heptanoate;
ethyl 7-(2-formyl-3-nitro-5-chlorophenyl)heptanoate;
ethyl 7-(2-nitro-3-formylphenyl)heptanoate;
ethyl 7-(2-nitro-3-formyl-4-fluorophenyl)heptanoate;
ethyl 7-(2-nitro-3-formyl-6-chlorophenyl)heptanoate;
ethyl 7-(2-nitro-3-formyl-5-methylphenyl)heptanoate;
ethyl 7-(3-nitro-4-formylphenyl)heptanoate;
ethyl 7-(3-nitro-4-formyl-5-methylphenyl)heptanoate;
ethyl 5-(2-formyl-3-nitrophenyl)oxypentanoate;
ethyl 5-(2-formyl-3-nitro-4-chlorophenyl)oxypentanoate;
ethyl 5-(2-formyl-3-nitro-4-methylphenyl)oxypentanoate;
ethyl 5-(2-formyl-3-nitro-6-methylphenyl)oxypentanoate;
ethyl 5-(3-formyl-4-nitro-5-chlorophenyl)oxypentanoate;
ethyl 5-(2-chloro-3-formyl-4-nitrophenyl)oxypentanoate;
ethyl 5-(3-formyl-4-nitrophenyl)oxypentanoate;
ethyl 5-(3-nitro-4-formylphenyl)oxypentanoate;
ethyl 5-(3-nitro-4-formyl-5-methylphenyl)oxypentanoate;
ethyl 5-(3-nitro-4-formyl-6-chlorophenyl)oxypentanoate;
ethyl 5-(3-formyl-4-nitro-6-chlorophenyl)oxypentanoate;
ethyl 5-(2-nitro-3-formylphenyl)oxypentanoate;
ethyl 5-(2-nitro-3-formyl-4-methylphenyl)oxypentanoate;
ethyl 5-(2-nitro-3-formyl-6-chlorophenyl)oxypentanoate;
ethyl 6-(2-formyl-3-nitrophenyl)oxyhexanoate;
ethyl 6-(2-formyl-3-nitro-4-chlorophenyl)oxyhexanoate;
ethyl 6-(2-formyl-3-nitro-6-chlorophenyl)oxyhexanoate;
ethyl 6-(3-formyl-4-nitrophenyl)oxyhexanoate;
ethyl 6-(3-formyl-4-nitro-6-chlorophenyl)oxyhexanoate;
ethyl 6-(3-formyl-4-nitro-5-methylphenyl)oxyhexanoate;
ethyl 6-(2-nitro-3-formylphenyl)oxyhexanoate;
ethyl 6-(2-nitro-3-formyl-6-fluorophenyl)oxyhexanoate;
ethyl 6-(2-nitro-3-formyl-5-methylphenyl)oxyhexanoate;
ethyl 6-(3-nitro-4-formylphenyl)oxyhexanoate;
ethyl 6-(3-nitro-4-formyl-6-methylphenyl)oxyhexanoate;
ethyl 6-(3-nitro-4-formyl-5-chlorophenyl)oxyhexanoate;
ethyl 2-(2-chloro-3-formyl-4-nitrophenyl)oxyacetate;
ethyl 2-(3-formyl-4-nitrophenyl)oxyacetate;
ethyl 2-(3-formyl-4-nitro-5-chlorophenyl)oxyacetate;
ethyl 2-(2-chloro-4-nitro-5-formylphenyl)oxyacetate; and
ethyl 2-(3-formyl-4-nitro-5-fluorophenyl)oxyacetate.

PREPARATION 4

Ester hydrolysis to give the acids of Formula 4 is described herein.

To a solution of ethyl 4-(3-formyl-4-nitrophenyl)oxybutyrate (65 g) in ethanol (400 ml) was added 3N NaOH (100 ml) in small portions. After 30 minutes at room temperature the reaction mixture was acidified with concentrated HCl and the ethanol evaporated. The aqueous residue was extracted with ethyl acetate (4×200 ml). The combined organic layers were washed with brine (2×200 ml), dried over Na2SO4, filtered and evaporated to give a light yellow solid. Trituration with ether afforded 4-(3-formyl-4-nitrophenyl)oxybutyric acid (55 g), m.p. 109°–110° C.

Following the above procedure, the esters prepared as per Preparation 1 are converted to the corresponding acid.

PREPARATION 5

Conversion of the acids of Formula 4 in Reaction Scheme A to the acid halide, preferably the chloride, preparatory to forming the amide compounds of Formula 6 was carried out as follows:

To a stirred suspension of 4-(3-formyl-4-nitrophenyl)oxybutyric acid (12.65 g) in benzene (50 ml) and dimethylformamide (0.5 ml) was added oxalyl chloride (4.40 ml) in small portions. When all the acid had been dissolved, the mixture was stirred for an additional 30 minutes. Evaporation of the solvent gave a thick syrup which was redissolved in dry tetrahydrofuran (50 ml) and reevaporated twice. The final residue of crude acid chloride was dissolved in tetrahydrofuran (50 ml) and used without further purification in the next reaction step.

Proceeding in a similar manner, the acids prepared as per Preparation 2 are converted to the corresponding acid chloride.

PREPARATION 6

Preparation of the acetates represented by Formula 6 is carried out by the following reaction.

A tetrahydrofuran solution of 4-(3-formyl-4-nitrophenyl)oxybutyric acid chloride was added dropwise to a solution of methyl N-cyclohexylglycinate (12.6 g, 50 mmol), triethylamine (9.0 ml) and 4-dimethylaminopyridine (0.6 g) in dry tetrahydrofuran (250 ml). When addition of the acid chloride was complete the reaction was stirred at room temperature for 1 hour. The mixture was evaporated, the residue dissolved in ethyl acetate, and the organic layer washed in 1M HCl three times, with brine twice and dried over Na2SO4, filtered and evaporated to give methyl 2-(N-cyclohexyl-4-(3-formyl-4-nitrophenyl)oxybutyramid-1-yl)acetate as a thick syrup.

Using this procedure and substituting the appropriate secondary amine and acid chloride for those described, there may be prepared the following representative compounds:

methyl 2-(N-cyclohexyl-4-(3-formyl-4-nitrophenyl)oxybutyramidyl)acetate;
methyl 2-(N-cyclohexylmethyl-4-(3-formyl-4-nitrophenyl)oxybutyramidyl)acetate;
methyl 2-(N-hexyl-4-(3-formyl-4-nitrophenyl)oxybutyramidyl)acetate;
methyl 2-(N-methyl-4-(3-formyl-4-nitrophenyl)oxybutyramidyl)acetate;
methyl 2-(N-ethyl-4-(3-formyl-4-nitrophenyl)oxybutyramidyl)acetate;
methyl 2-(N-pentyl-4-(3-formyl-4-nitrophenyl)oxybutyramidyl)acetate;

methyl 2-(N-cyclopentyl-4-(3-formyl-4-nitrophenyl)oxybutyramidyl)acetate;
methyl 2-(N-cyclopropylmethyl-4-(3-formyl-4-nitrophenyl)oxybutyramidyl)acetate;
methyl 2-(N-cycloheptyl-4-(3-formyl-4-nitrophenyl)oxybutyramidyl)acetate;
methyl 2-(N-cyclopentylbutyl-4-(3-formyl-4-nitrophenyl)oxybutyramidyl)acetate;
methyl 2-(N-cyclopentylmethyl-4-(3-formyl-4-nitrophenyl)oxybutyramidyl)acetate;
methyl 2-(N-phenyl-4-(3-formyl-4-nitrophenyl)oxybutyramidyl)acetate;
methyl 2-(N-benzyl-4-(3-formyl-4-nitrophenyl)oxybutyramidyl)acetate;
methyl 2-(N-diphenylmethyl-4-(3-formyl-4-nitrophenyl)oxybutyramidyl)acetate;
methyl 2-(N-cyclohexyl-4-(2-formyl-3-nitrophenyl)oxybutyramidyl)acetate;
methyl 2-(N-n-hexyl-4-(2-formyl-3-nitrophenyl)oxybutyramidyl)acetate;
methyl 2-(N-methyl-4-(2-formyl-3-nitrophenyl)oxybutyramidyl)acetate;
methyl 2-(N-phenyl-4-(2-formyl-3-nitrophenyl)oxybutyramidyl)acetate;
methyl 2-(N-benzyl-4-(2-formyl-3-nitrophenyl)oxybutyramidyl)acetate;
methyl 2-(N-phenyl-4-(2-nitro-3-formylphenyl)oxybutyramidyl)acetate;
methyl 2-(N-cyclohexyl-4-(2-nitro-3-formylphenyl)oxybutyramidyl)acetate;
methyl 2-(N-methyl-4-(2-nitro-3-formylphenyl)oxybutyramidyl)acetate;
methyl 2-(N-benzyl-4-(2-nitro-3-formylphenyl)oxybutyramidyl)acetate;
methyl 2-(N-cyclohexyl-4-(3-nitro-4-formylphenyl)oxybutyramidyl)acetate;
methyl 2-(N-methyl-4-(3-nitro-4-formylphenyl)oxybutyramidyl)acetate;
methyl 2-(N-n-hexyl-4-(3-nitro-4-formylphenyl)oxybutyramidyl)acetate;
methyl 2-(N-phenyl-4-(3-nitro-4-formylphenyl)oxybutyramidyl)acetate;
methyl 2-(N-benzyl-4-(3-nitro-4-formylphenyl)oxybutyramidyl)acetate;
methyl 2-(N-diphenylmethyl-4-(3-nitro-4-formylphenyl)oxybutyramidyl)acetate;
methyl 2-(N-cyclohexyl-4-(3-formyl-4-nitrophenyl)oxybutyramidyl)hexanate;
methyl 2-(N-cyclohexyl-4-(3-formyl-4-nitrophenyl)oxybutyramidyl)hexanate;
methyl 2-(N-cyclohexylmethyl-4-(3-formyl-4-nitrophenyl)oxybutyramidyl)hexanate;
methyl 2-(N-hexyl-4-(3-formyl-4-nitrophenyl)oxybutyramidyl)hexanate;
methyl 2-(N-methyl-4-(3-formyl-4-nitrophenyl)oxybutyramidyl)hexanate;
methyl 2-(N-ethyl-4-(3-formyl-4-nitrophenyl)oxybutyramidyl)hexanate;
methyl 2-(N-cyclohexyl-7-(3-formyl-4-nitrophenyl)oxyheptanamidyl)acetate;
methyl 2-(N-benzyl-7-(3-formyl-4-nitrophenyl)oxyheptanamidyl)acetate;
methyl 2-(N-methyl-7-(3-formyl-4-nitrophenyl)oxyheptanamidyl)acetate;
methyl 2-(N-diphenylmethyl-7-(3-formyl-4-nitrophenyl)oxyheptanamidyl)acetate;
methyl 2-(N-cyclohexyl-7-(2-formyl-3-nitro-4-chlorophenyl)oxyheptanamidyl)acetate;
methyl 2-(N-methyl-7-(2-formyl-3-nitrophenyl)oxyheptanamidyl)acetate;
methyl 2-(N-n-butyl-7-(2-formyl-3-nitrophenyl)oxyheptanamidyl)acetate;
methyl 2-(N-phenyl-7-(2-formyl-3-nitrophenyl)oxyheptanamidyl)acetate;
methyl 2-(N-methyl-7-(2-formyl-3-nitrophenyl)oxyheptanamidyl)acetate;
methyl 2-(N-benzyl-7-(2-formyl-3-nitrophenyl)oxyheptanamidyl)acetate;
methyl 2-(N-phenyl-7-(2-nitro-3-formylphenyl)oxyheptanamidyl)acetate;
methyl 2-(N-methyl-7-(2-nitro-3-formylphenyl)oxyheptanamidyl)acetate;
methyl 2-(N-cyclohexyl-7-(2-nitro-3-formylphenyl)oxyheptanamidyl)acetate;
methyl 2-(N-n-butyl-7-(3-nitro-4-formylphenyl)oxyheptanamidyl)acetate;
methyl 2-(N-benzyl-7-(3-nitro-4-formylphenyl)oxyheptanamidyl)acetate;
methyl 2-(N-cyclohexyl-5-(3-formyl-4-nitrophenyl)oxypentanamidyl)acetate;
methyl 2-(N-methyl-5-(3-formyl-4-nitrophenyl)oxypentanamidyl)acetate;
methyl 2-(N-hexyl-5-(3-formyl-4-nitrophenyl)oxypentanamidyl)acetate;
methyl 2-(N-cyclopentyl-5-(3-formyl-4-nitrophenyl)oxypentanamidyl)acetate;
methyl 2-(N-methyl-5-(3-formyl-4-nitrophenyl)oxypenamidyl)acetate;
methyl 2-(N-benzyl-5-(3-formyl-4-nitrophenyl)oxypentamidyl)acetate;
methyl 2-(N-cyclohexyl-5-(2-formyl-3-nitro-4-chlorophenyl)oxypentamidyl)acetate;
methyl 2-(N-methyl-5-(2-formyl-3-nitrophenyl)oxypentanamidyl)acetate;
methyl 2-(N-hexyl-5-(2-nitro-3-formylphenyl)oxypentanamidyl)acetate;
methyl 2-(N-phenyl-5-(2-nitro-3-formylphenyl)oxypentanamidyl)acetate;
methyl 2-(N-diphenylmethyl-5-(2-nitro-3-formylphenyl)oxypentanamidyl)acetate;
methyl 2-(N-cyclohexyl-5-(3-nitro-4-formylphenyl)oxypentanamidyl)acetate;
methyl 2-(N-methyl-5-(3-nitro-4-formylphenyl)oxypentanamidyl)acetate;
methyl 2-(N-phenyl-5-(3-nitro-4-formylphenyl)oxypentanamidyl)acetate;
methyl 2-(N-hexyl-2-(3-formyl-4-nitrophenyl)oxyacetamidyl)acetate;
methyl 2-(N-phenyl-2-(3-formyl-4-nitrophenyl)oxyacetamidyl)acetate;
methyl 2-(N-cyclohexyl-2-(2-formyl-3-nitro-4-chlorophenyl)oxyacetamidyl)acetate;
methyl 2-(N-methyl-2-(2-formyl-3-nitrophenyl)oxyacetamidyl)acetate;
methyl 2-(N-hexyl-2-(2-formyl-3-nitrophenyl)oxyacetamidyl)acetate;
methyl 2-(N-phenyl-2-(2-formyl-3-nitrophenyl)oxyacetamidyl)acetate;
methyl 2-(N-phenyl-2-(2-nitro-3-formylphenyl)oxyacetamidyl)acetate;
methyl 2-(N-cyclohexyl-2-(2-nitro-3-formylphenyl)oxyacetamidyl)acetate;
methyl 2-(N-methyl-2-(2-nitro-3-formylphenyl)oxyacetamidyl)acetate;
methyl 2-(N-benzyl-2-(2-nitro-3-formylphenyl)oxyacetamidyl)acetate;

methyl 2-(N-cyclopentyl-2-(3-nitro-4-formylphenyl)ox-yacetamidyl)acetate;
methyl 2-(N-cyclohexyl-2-(3-nitro-4-formylphenyl)ox-yacetamidyl)acetate;
methyl 2-(N-methyl-2-(3-nitro-4-formylphenyl)ox-yacetamidyl)acetate;
methyl 2-(N-cyclohexyl-6-(3-formyl-4-nitrophenyl)ox-yhexanamidyl)acetate;
methyl 2-(N-phenyl-6-(3-formyl-4-nitrophenyl)oxyhex-anamidyl)acetate;
methyl 2-(N-hexyl-6-(3-formyl-4-nitrophenyl)oxyhex-anamidyl)acetate;
methyl 2-(N-cyclohexyl-6-(2-formyl-3-nitro-4-chloro-phenyl)oxyhexanamidyl)acetate;
methyl 2-(N-hexyl-6-(2-formyl-3-nitrophenyl)oxyhex-anamidyl)acetate;
methyl 2-(N-methyl-6-(2-formyl-3-nitrophenyl)oxyhex-anamidyl)acetate;
methyl 2-(N-phenyl-6-(2-formyl-3-nitrophenyl)oxyhex-anamidyl)acetate;
methyl 2-(N-benzyl-6-(2-formyl-3-nitrophenyl)oxyhex-anamidyl)acetate;
methyl 2-(N-cyclohexyl-6-(2-nitro-3-formylphenyl)ox-yhexanamidyl)acetate;
methyl 2-(N-benzyl-6-(2-nitro-3-formylphenyl)oxyhex-anamidyl)acetate;
methyl 2-(N-methyl-6-(2-nitro-3-formylphenyl)oxyhex-anamidyl)acetate;
methyl 2-(N-cyclopentyl-6-(3-nitro-4-formylphenyl)ox-yhexanamidyl)acetate;
methyl 2-(N-methyl-6-(3-nitro-4-formylphenyl)oxyhex-anamidyl)acetate; and
methyl 2-(N-benzyl-6-(3-nitro-4-formylphenyl)oxyhex-anamidyl)acetate.

PREPARATION 7

Preparation of the acetamides represented by Formula 6 is illustrated herein.

A solution of 4-(3-formyl-4-nitrophenyl)oxybutyric acid chloride was added dropwise to a solution of N-cyclohexyl glycinamide (7.8 g) and sodium carbonate (6.90 g) in aqueous tetrahydrofuran cooled to 5° C. The reaction was stirred at room temperature for 1 hour, then extracted with ethyl acetate. The organic extract was washed with saturated sodium bicarbonate three times, 3×1M HCl and 2×brine, filtered and the solvent evaporated to give 2-(N-cyclohexyl-4-(3-formyl-4-nitrophenyl)oxybutyramidyl)acetamide as a solid, m.p. 104°–105° C. Similarly, treatment of cyclohexyl $R_7R_8$-N-substituted acetamides from Preparation 2 gives the corresponding 2-(N-cyclohexyl-4-(3-nitro-4-formyl-phenyl)oxybutyramidyl-$R_7R_8$-N-substituted acetamides.

Using this procedure and substituting the amide of the secondary amine and the appropriate acid chloride, there may be prepared the amide analogues of the representative compounds set forth in preparation 6.

PREPARATION 8

Compounds wherein $R_1$ is alkyl are prepared by a two step process the first of which is as follows. (The second step is described in Preparation 9.)

Into a tetrahydrofuran solution of methyl Grignard reagent (120 mmol), either purchased from commercial sources or freshly generated from the corresponding halide and elemental magnesium, was added dropwise a solution of methyl 2-(N-cyclohexyl-4-(3-formyl-4-nitrophenyl)oxybutyramid-1-yl)acetate (35 g) in tetrahydrofuran (200 ml). The resulting mixture was warmed to reflux for one hour, then cooled and quenched with saturated aqueous ammonium chloride. Evaporation of the tetrahydrofuran followed by extraction with ethyl acetate provided methyl 2-(N-cyclohexyl-4-(3-(1-hydroxyethyl)-4-nitrophenyl)oxybutyramidyl)acetate (30 g).

Proceeding in a similar manner, but substituting the the appropriate reagents and a compound whose preparation is described in Preparation 6, all the compounds of Preparation 6 are converted to their corresponding 1-hydroxyethyl analog.

PREPARATION 9

Oxidation of the secondary alcohols from Preparation 8 is carried out by the following method.

Anhydrous chromium trioxide, 8 g, was added to a stirred solution of 60 ml of dry pyridine in 200 ml of dry dichloromethane and stirred under a dry nitrogen atmosphere at about 20° C. for 15 minutes. A solution of 27 g of methyl 2-(N-cyclohexyl-4-(3-(1-hydroxyethyl)-4-nitrophenyl)oxybutyramid-1-yl)acetate in 150 ml of dry dichloromethane was added and the reaction mixture stirred for an additional 30 minutes at room temperature. The solution was decanted from the residue and the residue washed with two 100 ml of dry diethyl ether. The organic solutions are combined, washed successively with two 200 ml portions of water and dried over anhydrous sodium sulphate. Evaporation of the solvent under reduced pressure gives a residue which is crystallized from ethyl acetate to give methyl 2-(N-cyclohexyl-4-[(3-(ethan-1-on)-4-nitrophenyl)oxy]-butyramidyl)acetate.

Proceeding in a similar manner, the secondary alcohols of obtained by the reaction in Preparation 5 may be converted to their corresponding ketone using the above reagents but substituting the appropriate secondary alcohol for methyl 2-(N-cyclohexyl-4-(3-(1-hydroxyethyl)-4-nitrophenyl)oxybutyramidyl)acetate.

PREPARATION 10

Preparation of methyl 2-(N-cyclohexyl-4-(2-carboxy-3-nitrophenyl)oxybutyramidyl)acetate and analogues as illustrated by Formula (11) in Reaction Scheme B.

To a solution of methyl 2-(N-cyclohexyl-4-(3-formyl-4-nitrophenyl)oxybutyramidyl)acetate (3.5 g) in dry pyridine (20 ml) under a blanket of nitrogen was added solid tetra-N-butylammonium permanganate portionwise over 1 hour. The reaction was stirred at room temperature for 1 hour and was then poured into ethyl acetate/6M hydrogen chloride (100 ml each). Solid sodium bisulfite was added to decolorize the solution and the layers were separated. The aqueous layer was washed with ethyl acetate (2×50 ml). The combined organic layers were washed with 1M HCl (3×50 ml) and brine (2×50 ml), dried, filtered and evaporated to give a syrup which foamed at high vacuum from dichloromethane to yield methyl 2-(N-cyclohexyl-4-(3-carboxy-4-nitrophenyl)oxybutyramidyl)acetate.

Following this procedure, all of the aldehydes of Preparation 6 are converted to the corresponding acid.

PREPARATION 11

Reduction of the nitroacid compounds from Preparation 10 to their anthranilic acid analogue is carried out using the following reagents and conditions.

Methyl 2-(N-cyclohexyl-4-(3-carboxy-4-nitrophenyl)oxybutyramidyl)acetate (78.7 g) was dissolved in absolute ethanol (750 ml) and hydrogenated at 60 psi over 10% Pd-C (6 g) overnight. The catalyst was removed by filtration through a pad of Celite, and was thoroughly washed with additional ethanol (250 ml). The combined filtrates were thoroughly evaporated to give a thick syrup which crystallized from hexane/dichloromethane to afford methyl 2-(N-cyclohexyl-4-(3-carboxy-2-aminophenyl)oxybutyramidyl)acetate.

Proceeding in a similar manner, but substituting the appropriate nitroacid for methyl 2-(N-cyclohexyl-4-(3-carboxy-4-nitrophenyl)oxybutyramidyl)acetate, nitroacids prepared as per Preparation 10 may be reduced to their corresponding amine.

PREPARATION 12

Ethyl 4-(2-oxo-1,2,3,5-tetrahydroimadazo[2,1-b]quinazolin-7-yl)oxybutyrate

To a solution of 7-hydroxy-1,2,3,5-tetrahydroimidazo[2,1-b]quinazolin-2-one (2.6 g) made as per U.S. Pat. No. 3,932,407 and ethyl 4-bromobutyrate (1.72 ml) in 100 ml dimethylformamide was added 1.86 g potassium carbonate. The reaction mixture was sealed under a blanket of nitrogen and heated to 100° C. for 4 hours. The reaction mixture was cooled, poured into 100 ml of water, and the resulting precipitate collected by filtration. Recrystallization from dimethylformamide-water gave ethyl 4-(2-oxo-1,2,3,5-tetrahydroimidazo[2,1-b]quinazolin-7-yl)oxybutyrate, m.p. 243°-244° C.

PREPARATION 13

4-(2-oxo-1,2,3,5-tetrahydroimidazo[2,1-b]quinazolin-7-yl)oxybutyric acid

To a suspension of ethyl 4-(2-oxo-1,2,3,5-tetrahydroimidazo[2,1-b]quinazolin-7-yl)oxybutyrate (65 g) in ethanol (1000 ml) was added 3N NaOH (100 ml) in small portions. After 30 minutes at room temperature the reaction mixture was acidified with concentrated HCl. The resulting thick precipitate was collected by filtration and/or centrifugation and dried to give 4-(2-oxo-1,2,3,5-tetrahydroimadazo[2,1-b]quinazolin-7-yl)oxybutyric acid (m.p. >300° C.) quantitatively.

Esters prepared as per Preparation 12 above all may be converted to their corresponding acid by the foregoing method.

EXAMPLE 1

Methyl 2-(N-cyclohexyl-4-(2-oxo-1,2,3,5-tetrahydroimidazo[2,1-b]quinazolin-7-yl)oxybutyramidyl)acetate and corresponding acetamide Methyl 2-(N-cyclohexyl-4-(3-formyl-4-nitrophenyl)oxybutyramidyl)acetate (12.5 g) was added to a solution of glycine ethyl ester hydrochloride (44.7 g) and sodium acetate (21 g) in methanol and stirred for 1 hour. Sodium cyanoborohydride (1.21 g) was added and the mixture was stirred for 30 minutes. The crude acetate was isolated by filtering the solution, evaporating the solvent, dissolving the residue in ethyl acetate which was washed with dilute base and brine, dried and evaporated to give a thick syrup. This syrup was taken up in ethanol (300 ml) and reduced with 10% palladium on carbon (2 g). The catalyst was filtered out and the combined filtrates treated sequentially with cyanogen bromide (3.73 g) followed by ammonium hydroxide to yield methyl-2-(N-cyclohexyl-4-(2-oxo-1,2,3,5-tetrahydroimidazo[2,1-b]quinazolin-7-yl)oxybutyramidyl)acetate, m.p. 185°-186° C.

Proceeding in the same manner but substituting the appropriate ester or acetamide for methyl 2-(N-cyclohexyl-4-(3-formyl-4-nitrophenyl)oxybutyamide)acetate all the nitroaldehyde compounds of Preparation 6 or Preparation 7 are similarly converted to their corresponding substituted 2-oxo-1,2,3,5-tetrahydroimidazo[2,1-b]quinazoline-based alkyl ester or amide, examples of which are:

Esters:

methyl 2-(N-cyclohexylmethyl-4-(2-oxo-1,2,3,5-tetrahydroimidazo[2,1-b]quinazolin-7-yl)oxybutyramidyl)acetate;

methyl 2-(N-methyl-4-(2-oxo-1,2,3,5-tetrahydroimidazo[2,1-b]quinazolin-7-yl)oxybutyramidyl)acetate;

methyl 2-(N-hexyl-4-(2-oxo-1,2,3,5-tetrahydroimidazo[2,1-b]quinazolin-7-yl)oxybutyramidyl)acetate;

methyl 2-(N-phenyl-4-(2-oxo-1,2,3,5-tetrahydroimidazo[2,1-b]quinazolin-7-yl)oxybutyramidyl)acetate;

methyl 2-(N-cyclohexyl-4-(2-oxo-5-methyl-1,2,3,5-tetrahydroimidazo[2,1-b]quinazolin-7-yl)oxybutyramidyl)acetate;

methyl 2-(N-methyl-4-(2-oxo-3-methyl-1,2,3,5-tetrahydroimidazo[2,1-b]quinazolin-7-yl)oxybutyramidyl)acetate;

hexyl 2-(N-cyclohexyl-4-(2-oxo-1,2,3,5-tetrahydroimidazo[2,1-b]quinazolin-7-yl)oxybutyramidyl)acetate;

hexyl 2-(N-cyclohexylmethyl-4-(2-oxo-1,2,3,5-tetrahydroimidazo[2,1-b]quinazolin-7-yl)oxybutyramidyl)acetate;

hexyl 2-(N-methyl-4-(2-oxo-1,2,3,5-tetrahydroimidazo[2,1-b]quinazolin-7-yl)oxybutyramidyl)acetate;

hexyl 2-(N-hexyl-4-(2-oxo-1,2,3,5-tetrahydroimidazo[2,1-b]quinazolin-7-yl)oxybutyramidyl)acetate;

hexyl 2-(N-phenyl-4-(2-oxo-1,2,3,5-tetrahydroimidazo[2,1-b]quinazolin-7-yl)oxybutyramidyl)acetate;

hexyl 2-(N-cyclohexyl-4-(2-oxo-5-methyl-1,2,3,5-tetrahydroimidazo[2,1-b]quinazolin-7-yl)oxybutyramidyl)acetate;

hexyl 2-(N-methyl-4-(2-oxo-3-methyl-1,2,3,5-tetrahydroimidazo[2,1-b]quinazolin-7-yl)oxybutyramidyl)acetate;

methyl 2-(N-cyclohexyl-4-(2-oxo-1,2,3,5-tetrahydroimidazo[2,1-b]quinazolin-7-yl)oxybutyramidyl)hexanoate;

methyl 2-(N-cyclohexylmethyl-4-(2-oxo-1,2,3,5-tetrahydroimidazo[2,1-b]quinazolin-7-yl)oxybutyramidyl)hexanoate;

methyl 2-(N-methyl-4-(2-oxo-1,2,3,5-tetrahydroimidazo[2,1-b]quinazolin-7-yl)oxybutyramidyl)hexanoate;

methyl 2-(N-hexyl-4-(2-oxo-1,2,3,5-tetrahydroimidazo[2,1-b]quinazolin-7-yl)oxybutyramidyl)hexanoate;

methyl 2-(N-phenyl-4-(2-oxo-1,2,3,5-tetrahydroimidazo[2,1-b]quinazolin-7-yl)oxybutyramidyl)hexanoate;

methyl 2-(N-cyclohexyl-4-(2-oxo-5-methyl-1,2,3,5-tetrahydroimidazo[2,1-b]quinazolin-7-yl)oxybutyramidyl)hexanoate;

methyl 2-(N-methyl-4-(2-oxo-3-methyl-1,2,3,5-tetrahydroimidazo[2,1-b]quinazolin-7-yl)oxybutyramidyl)hexanoate.

Amides:

2-(N-cyclohexyl-4-(2-oxo-1,2,3,5-tetrahydroimidazo[2,1-b]quinazolin-7-yl)oxybutyramidyl)acetamide, m.p. 207°–208° C.;

2-(N-cyclohexylmethyl-4-(2-oxo-1,2,3,5-tetrahydroimidazo[2,1-b]quinazolin-7-yl)oxybutyramidyl)acetamide;

2-(N-methyl-4-(2-oxo-1,2,3,5-tetrahydroimidazo-[2,1-b]quinazolin-7-yl)oxybutyramidyl)acetamide;

2-(N-hexyl-4-(2-oxo-1,2,3,5-tetrahydroimidazo[2,1-b]quinazolin-7-yl)oxybutyramidyl)acetamide;

2-(N-phenyl-4-(2-oxo-1,2,3,5-tetrahydroimidazo-[2,1-b]quinazolin-7-yl)oxybutyramidyl)acetamide;

2-(N-cyclohexyl-4-(2-oxo-5-methyl-1,2,3,5-tetrahydroimidazo[2,1-b]quinazolin-7-yl)oxybutyramidyl)acetamide;

2-(N-methyl-4-(2-oxo-3-methyl-1,2,3,5-tetrahydroimidazo[2,1-b]quinazolin-7-yl)oxybutyramidyl)acetamide;

2-(N-cyclohexyl-4-(2-oxo-1,2,3,5-tetrahydroimidazo[2,1-b]quinazolin-7-yl)oxybutyramidyl)N,N-dimethylacetamide;

2-(N-cyclohexylmethyl-4-(2-oxo-1,2,3,5-tetrahydroimidazo[2,1-b]quinazolin-7-yl)oxybutyramidyl)N,N-dimethyl-acetamide;

2-(N-methyl-4-(2-oxo-1,2,3,5-tetrahydroimidazo-[2,1-b]quinazolin-7-yl)oxybutyramidyl)N,N-dimethyl-acetamide;

2-(N-hexyl-4-(2-oxo-1,2,3,5-tetrahydroimidazo[2,1-b]quinazolin-7-yl)oxybutyramidyl)N,N-dimethyl-acetamide;

2-(N-phenyl-4-(2-oxo-1,2,3,5-tetrahydroimidazo-[2,1-b]quinazolin-7-yl)oxybutyramidyl)N,N-dimethyl-acetamide;

2-(N-cyclohexyl-4-(2-oxo-5-methyl-1,2,3,5-tetrahydroimidazo[2,1-b]quinazolin-7-yl)oxybutyramidyl)-N,N-dimethyl-acetamide;

2-(N-methyl-4-(2-oxo-3-methyl-1,2,3,5-tetrahydroimidazo[2,1-b]quinazolin-7-yl)oxybutyramidyl)-N,N-dimethyl-acetamide;

2-(N-cyclohexyl-4-(2-oxo-1,2,3,5-tetrahydroimidazo[2,1-b]quinazolin-7-yl)oxybutyramidyl)-hexanimide;

2-(N-cyclohexylmethyl-4-(2-oxo-1,2,3,5-tetrahydroimidazo[2,1-b]quinazolin-7-yl)oxybutyramidyl)-hexanamide;

2-(N-methyl-4-(2-oxo-1,2,3,5-tetrahydroimidazo-[2,1-b]quinazolin-7-yl)oxybutyramidyl)hexanamide;

2-(N-hexyl-4-(2-oxo-1,2,3,5-tetrahydroimidazo[2,1-b]quinazolin-7-yl)oxybutyramidyl)hexanamide;

2-(N-phenyl-4-(2-oxo-1,2,3,5-tetrahydroimidazo-[2,1-b]quinazolin-7-yl)oxybutyramidyl)hexanamide;

2-(N-cyclohexyl-4-(2-oxo-5-methyl-1,2,3,5-tetrahydroimidazo[2,1-b]quinazolin-7-yl)oxybutyramidyl)-hexanamide;

2-(N-methyl-4-(2-oxo-3-methyl-1,2,3,5-tetrahydroimidazo[2,1-b]quinazolin-7-yl)oxybutyramidyl)-hexanamide;

2-(N-cyclohexyl-4-(2-oxo-1,2,3,5-tetrahydroimidazo[2,1-b]quinazolin-7-yl)oxybutyramidyl)N-methyl-N-ethyl-acetamide;

2-(N-cyclohexylmethyl-4-(2-oxo-1,2,3,5-tetrahydroimidazo[2,1-b]quinazolin-7-yl)oxybutyramidyl)-N-methyl-N-ethyl-acetamide;

2-(N-methyl-4-(2-oxo-1,2,3,5-tetrahydroimidazo-[2,1-b]quinazolin-7-yl)oxybutyramidyl)-N-methyl-N-ethyl-acetamide;

2-(N-hexyl-4-(2-oxo-1,2,3,5-tetrahydroimidazo[2,1-b]quinazolin-7-yl)oxybutyramidyl)N-methyl-N-ethyl-acetamide;

2-(N-phenyl-4-(2-oxo-1,2,3,5-tetrahydroimidazo-[2,1-b]quinazolin-7-yl)oxybutyramidyl)N-methyl-N-ethyl-acetamide;

2-(N-cyclohexyl-4-(2-oxo-5-methyl-1,2,3,5-tetrahydroimidazo[2,1-b]quinazolin-7-yl)oxybutyramidyl)-N-methyl-N-ethyl-acetamide;

2-(N-cyclohexyl-4-(2-oxo-1,2,3,5-tetrahydroimidazo[2,1-b]quinazolin-7-yl)oxybutyramidyl)N-methylacetamide;

2-(N-cyclohexylmethyl-4-(2-oxo-1,2,3,5-tetrahydroimidazo[2,1-b]quinazolin-7-yl)oxybutyramidyl)N-methyl-acetamide;

2-(N-methyl-4-(2-oxo-1,2,3,5-tetrahydroimidazo-[2,1-b]quinazolin-7-yl)oxybutyramidyl)N-methyl-acetamide;

2-(N-hexyl-4-(2-oxo-1,2,3,5-tetrahydroimidazo[2,1-b]quinazolin-7-yl)oxybutyramidyl)N-methyl-acetamide;

2-(N-phenyl-4-(2-oxo-1,2,3,5-tetrahydroimidazo-[2,1-b]quinazolin-7-yl)oxybutyramidyl)N-methyl-acetamide;

2-(N-cyclohexyl-4-(2-oxo-5-methyl-1,2,3,5-tetrahydroimidazo[2,1-b]quinazolin-7-yl)oxybutyramidyl)-N-methyl-acetamide;

2-(N-methyl-4-(2-oxo-3-methyl-1,2,3,5-tetrahydroimidazo[2,1-b]quinazolin-7-yl)oxybutyramidyl)-N-methyl-acetamide; and 2-(N-methyl-4-(2-oxo-3-methyl-1,2,3,5-tetrahydroimidazo[2,1-b]quinazolin-7-yl)oxybutyramidyl)-N,N-dimethyl-acetamide.

EXAMPLE 2

2-(N-cyclohexyl-4-(2-oxo-1,2,3,5-tetrahydroimidazo[2,1-b]quinazolin-7-yl)oxybutyramidyl)acetic acid A suspension of methyl 2-(N-cyclohexyl-4-(2-oxy-1,2,3,5-tetrahydroimidazo[2,1-b]quinazolin-7-yl)-oxybutyramidyl)acetate (8.1 g) in 50 ml of methanol was treated with 45 ml of 2N NaOH. The resulting solution was filtered to remove trace insoluble materials and then acidified to pH 5. The precipitated product was collected by filtration and dried to give 2-(N-cyclohexyl-4-(2-oxo-1,2,3,5-tetrahydroimidazo[2,1-b]quinazolin-7-yl)oxybutyramidyl)acetic acid, m.p. 194°–195° C.

Proceeding in the same manner the esters prepared in Example 1 may be converted to their corresponding acid of which the following are examples:

2-(N-cyclohexylmethyl-4-(2-oxo-1,2,3,5-tetrahydroimidazo[2,1-b]quinazolin-7-yl)oxybutyramidyl)acetic acid;

2-(N-methyl-4-(2-oxo-1,2,3,5-tetrahydroimidazo[2,1-b]quinazolin-7-yl)oxybutyramidyl)acetic acid;

2-(N-hexyl-4-(2-oxo-1,2,3,5-tetrahydroimidazo[2,1-b]quinazolin-7-yl)oxybutyramidyl)acetic acid;

2-(N-phenyl-4-(2-oxo-1,2,3,5-tetrahydroimidazo[2,1-b]quinazolin-7-yl)oxybutyramidyl)acetic acid;

2-(N-cyclohexyl-4-(2-oxo-5-methyl-1,2,3,5-tetrahydroimidazo[2,1-b]quinazolin-7-yl)oxybutyramidyl)acetic acid;

2-(N-methyl-4-(2-oxo-3-methyl-1,2,3,5-tetrahydroimidazo[2,1-b]quinazolin-7-yl)oxybutyramidyl)acetic acid;

2-(N-cyclohexyl-4-(2-oxo-3-methyl-1,2,3,5-tetrahydroimidazo[2,1-b]quinazolin-7-yl)oxybutyramidyl)acetic acid;

2-(N-cyclohexyl-4-(2-oxo-6-chloro-1,2,3,5-tetrahydroimidazo[2,1-b]quinazolin-7-yl)oxybutyramidyl)acetic acid;

2-(N-cyclohexyl-4-(2-oxo-6-methoxy-1,2,3,5-tetrahydroimidazo[2,1-b]quinazolin-7-yl)oxybutyramidyl)acetic acid;

2-(N-cyclohexyl-4-(2-oxo-6-methyl-1,2,3,5-tetrahydroimidazo[2,1-b]quinazolin-7-yl)oxybutyramidyl)acetic acid;

2-(N-methyl-4-(2-oxo-6-chloro-1,2,3,5-tetrahydroimidazo[2,1-b]quinazolin-7-yl)oxybutyramidyl)acetic acid;

2-(N-benzyl-4-(2-oxo-1,2,3,5-tetrahydroimidazo[2,1-b]quinazolin-7-yl)oxybutyramidyl)acetic acid;

2-(N-cyclohexylbutyl-4-(2-oxo-1,2,3,5-tetrahydroimidazo[2,1-b]quinazolin-7-yl)oxybutyramidyl)acetic acid;

2-(N-cyclooctyl-4-(2-oxo-1,2,3,5-tetrahydroimidazo[2,1-b]quinazolin-7-yl)oxybutyramidyl)acetic acid;

2-(N-cyclopentyl-4-(2-oxo-1,2,3,5-tetrahydroimidazo[2,1-b]quinazolin-7-yl)oxybutyramidyl)acetic acid;

2-(N-cyclopentyl-4-(2-oxo-6-chloro-1,-2,3,5-tetrahydroimidazo[2,1-b]quinazolin-7-yl)oxybutyramidyl)acetic acid;

2-(N-cyclopentylmethyl-4-(2-oxo-1,2,3,5-tetrahydroimidazo[2,1-b]quinazolin-7-yl)oxybutyramidyl)acetic acid;

2-(N-diphenylmethyl-4-(2-oxo-1,2,3,5-tetrahydroimidazo[2,1-b]quinazolin-7-yl)oxybutyramidyl)acetic acid;

2-(N-methyl-4-(2-oxo-9-methyl-1,2,3,5-tetrahydroimidazo[2,1-b]quinazolin-7-yl)oxybutyramidyl)acetic acid;

2-(N-hexyl-4-(2-oxo-1,2,3,5-tetrahydroimidazo[2,1-b]quinazolin-7-yl)oxybutyramidyl)acetic acid;

2-(N-(4-chlorobenzyl)-4-(2-oxo-1,2,3,5-tetrahydroimidazo[2,1-b]quinazolin-7-yl)oxybutyramidyl)acetic acid;

2-(N-(4-methoxybenzyl)-4-(2-oxo-1,2,3,5-tetrahydroimidazo[2,1-b]quinazolin-7-yl)oxybutyramidyl)acetic acid;

2-(N-cyclohexyl-4-(2-oxo-1,2,3,5-tetrahydroimidazo[2,1-b]quinazolin-6-yl)oxybutyramidyl)acetic acid;

2-(N-cyclohexylbutyl-4-(2-oxo-1,2,3,5-tetrahydroimidazo[2,1-b]quinazolin-6-yl)oxybutyramidyl)acetic acid;

2-(N-cyclohexylmethyl-4-(2-oxo-1,2,3,5-tetrahydroimidazo[2,1-b]quinazolin-6-yl)oxybutyramidyl)acetic acid;

2-(N-phenyl-4-(2-oxo-1,2,3,5-tetrahydroimidazo[2,1-b]quinazolin-6-yl)oxybutyramidyl)acetic acid;

2-(N-cyclohexyl-4-(2-oxo-7-chloro-1,2,3,5-tetrahydroimidazo[2,1-b]quinazolin-6-yl)oxybutyramidyl)acetic acid;

2-(N-cyclohexyl-4-(2-oxo-7-methyl-1,2,3,5-tetrahydroimidazo[2,1-b]quinazolin-6-yl)oxybutyramidyl)acetic acid;

2-(N-cyclohexyl-4-(2-oxo-9-chloro-1,2,3,5-tetrahydroimidazo[2,1-b]quinazolin-6-yl)oxybutyramidyl)acetic acid;

2-(N-benzyl-4-(2-oxo-1,2,3,5-tetrahydroimidazo[2,1-b]-6-oxoquinazolin-6-yl)oxybutyramidyl)acetic acid;

2-(N-cyclopentyl-4-(2-oxo-1,2,3,5-tetrahydroimidazo[2,1-b]quinazolin-6-yl)oxybutyramidyl)acetic acid;

2-(N-cyclopentylmethyl-4-(2-oxo-1,2,3,5-tetrahydroimidazo[2,1-b]quinazolin-6-yl)oxybutyramidyl)acetic acid;

2-(N-diphenylmethyl-4-(2-oxo-1,2,3,5-tetrahydroimidazo[2,1-b]quinazolin-6-yl)oxybutyramidyl)acetic acid;

2-(N-(4-chlorobenzyl)-4-(2-oxo-1,2,3,5-tetrahydroimidazo[2,1-b]quinazolin-6-yl)oxybutyramidyl)acetic acid;

2-(N-(4-methyoxybenzyl)-4-(2-oxo-1,2,3,5-tetrahydroimidazo[2,1-b]quinazolin-6-yl)oxybutyramidyl)acetic acid;

2-(N-cyclohexyl-4-(2-oxo-1,2,3,5-tetrahydroimidazo[2,1-b]quinazolin-8-yl)oxybutyramidyl)acetic acid;

2-(N-cyclohexyl-4-(2-oxo-6-methyl-1,2,3,5-tetrahydroimidazo[2,1-b]quinazolin-8-yl)oxybutyramidyl)acetic acid;

2-(N-cyclohexylmethyl-4-(2-oxo-1,2,3,5-tetrahydroimidazo[2,1-b]quinazolin-8-yl)oxybutyramidyl)acetic acid;

2-(N-cyclohexyl-4-(2-oxo-6-chloro-1,2,3,5-tetrahydroimidazo[2,1-b]quinazolin-8-yl)oxybutyramidyl)acetic acid;

2-(N-cyclohexylbutyl-4-(2-oxo-1,2,3,5-tetrahydroimidazo[2,1-b]quinazolin-8-yl)oxybutyramidyl)acetic acid;

2-(N-methyl-4-(2-oxo-1,2,3,5-tetrahydroimidazo[2,1-b]quinazolin-8-yl)oxybutyramidyl)acetic acid;

2-(N-cyclohexyl-4-(2-oxo-7-chloro-1,2,3,5-tetrahydroimidazo[2,1-b]quinazolin-8-yl)oxybutyramidyl)acetic acid;

2-(N-cyclohexyl-4-(2-oxo-7-methyl-1,2,3,5-tetrahydroimidazo[2,1-b]quinazolin-8-yl)oxybutyramidyl)acetic acid;

2-(N-cyclohexyl-4-(2-oxo-9-chloro-1,2,3,5-tetrahydroimidazo[2,1-b]quinazolin-8-yl)oxybutyramidyl)acetic acid;

2-(N-benzyl-4-(2-oxo-1,2,3,5-tetrahydroimidazo[2,1-b]quinazolin-8-yl)oxybutyramidyl)acetic acid;

2-(N-cyclopentyl-4-(2-oxo-1,2,3,5-tetrahydroimidazo[2,1-b]quinazolin-8-yl)oxybutyramidyl)acetic acid;

2-(N-cyclopentylbutyl-4-(2-oxo-1,2,3,5-tetrahydroimidazo[2,1-b]quinazolin-8-yl)oxybutyramidyl)acetic acid;

2-(N-diphenylmethyl-4-(2-oxo-1,2,3,5-tetrahydroimidazo[2,1-b]quinazolin-8-yl)oxybutyramidyl)acetic acid;

2-(N-(4-chlorobenzyl)-4-(2-oxo-1,2,3,5-tetrahydroimidazo[2,1-b]quinazolin-8-yl)oxybutyramidyl)acetic acid;

2-(N-(4-methoxybenzyl)-4-(2-oxo-1,2,3,5-tetrahydroimidazo[2,1-b]quinazolin-8-yl)oxybutyramidyl)acetic acid;

2-(N-cyclopentyl-4-(2-oxo-1,2,3,5-tetrahydroimidazo[2,1-b]quinazolin-9-yl)oxybutyramidyl)acetic acid;
2-(N-phenyl-4-(2-oxo-1,2,3,5-tetrahydroimidazo[2,1-b]quinazolin-9-yl)oxybutyramidyl)acetic acid;
2-(N-cyclohexyl-4-(2-oxo-6-chloro-1,2,3,5-tetrahydroimidazo[2,1-b]quinazolin-9-yl)oxybutyramidyl)acetic acid;
2-(N-cyclohexylbutyl-4-(2-oxo-1,2,3,5-tetrahydroimidazo[2,1-b]quinazolin-9-yl)oxybutyramidyl)acetic acid;
2-(N-methyl-4-(2-oxo-1,2,3,5-tetrahydroimidazo[2,1-b]quinazolin-9-yl)oxybutyramidyl)acetic acid;
2-(N-hexyl-4-(2-oxo-1,2,3,5-tetrahydroimidazo[2,1-b]quinazolin-9-yl)oxybutyramidyl)acetic acid;
2-(N-benzyl-4-(2-oxy-1,2,3,5-tetrahydroimidazo[2,1-b]quinazolin-9-yl)oxybutyramidyl)acetic acid;
2-(N-cyclopentyl-4-(2-oxy-6-methyl-1,2,3,5-tetrahydroimidazo[2,1-b]quinazolin-9-yl)oxybutyramidyl)acetic acid;
2-(N-diphenylmethyl-4-(2-oxo-1,2,3,5-tetrahydroimidazo[2,1-b]quinazolin-9-yl)oxybutyramidyl)acetic acid;
2-(N-cyclohexyl-7-(2-oxo-1,2,3,5-tetrahydroimidazo[2,1-b]quinazolin-7-yl)oxyheptanamidyl)acetic acid;
2-(N-cyclohexylmethyl-7-(2-oxo-1,2,3,5-tetrahydroimidazo[2,1-b]quinazolin-7-yl)oxyheptanamidyl)acetic acid;
2-(N-phenyl-7-(2-oxo-1,2,3,5-tetrahydroimidazo[2,1-b]quinazolin-7-yl)oxyheptanamidyl)acetic acid;
2-(N-methyl-7-(2-oxo-5-methyl-1,2,3,5-tetrahydroimidazo[2,1-b]quinazolin-7-yl)oxyheptanamidyl)acetic acid;
2-(N-phenyl-7-(2-oxo-3-methyl-1,2,3,5-tetrahydroimidazo[2,1-b]quinazolin-7-yl)oxyheptanamidyl)acetic acid;
2-(N-cyclohexyl-7-(2-oxo-6-chloro-1,2,3,5-tetrahydroimidazo[2,1-b]quinazolin-7-yl)oxyheptanamidyl)acetic acid;
2-(N-cyclohexyl-7-(2-oxo-3-methyl-6-chloro-1,2,3,5-tetrahydroimidazo[2,1-b]quinazolin-7-yl)oxyheptanamidyl)acetic acid;
2-(N-cyclopentylbutyl-7-(2-oxo-1,2,3,5-tetrahydroimidazo[2,1-b]quinazolin-7-yl)oxyheptanamidyl)acetic acid;
2-(N-cyclohexyl-7-(2-oxo-6-methyl-1,2,3,5-tetrahydroimidazo[2,1-b]quinazolin-7-yl)oxyheptanamidyl)acetic acid;
2-(N-hexyl-7-(2-oxo-1,2,3,5-tetrahydroimidazo[2,1-b]quinazolin-7-yl)oxyheptanamidyl)acetic acid;
2-(N-cyclohexyl-7-(2-oxo-6-chloro-1,2,3,5-tetrahydroimidazo[2,1-b]quinazolin-7-yl)oxyheptanamidyl)acetic acid;
2-(N-cyclohexyl-7-(2-oxo-6-methoxy-1,2,3,5-tetrahydroimidazo[2,1-b]quinazolin-7-yl)oxyheptanamidyl)acetic acid;
2-(N-benzyl-7-(2-oxo-1,2,3,5-tetrahydroimidazo[2,1-b]quinazolin-7-yl)oxyheptanamidyl)acetic acid;
2-(N-cyclohexyl-7-(2-oxo-6-methoxy-1,2,3,5-tetrahydroimidazo[2,1-b]quinazolin-7-yl)oxyheptanamidyl)acetic acid;
2-(N-cyclopentyl-7-(2-oxo-6-chloro-1,2,3,5-tetrahydroimidazo[2,1-b]quinazolin-7-yl)oxyheptanamidyl)acetic acid;
2-(N-diphenylmethyl-7-(2-oxo-1,2,3,5-tetrahydroimidazo[2,1-b]quinazolin-7-yl)oxyheptanamidyl)acetic acid;
2-(N-(4-chlorobenzyl)-7-(2-oxo-1,2,3,5-tetrahydroimidazo[2,1-b]quinazolin-7-yl)oxyheptanamidyl)acetic acid;
2-(N-(4-methoxybenzyl)-7-(2-oxo-1,2,3,5-tetrahydroimidazo[2,1-b]quinazolin-7-yl)oxyheptanamidyl)acetic acid;
2-(N-cyclohexylbutyl-7-(2-oxo-1,2,-3,5-tetrahydroimidazo[2,1-b]quinazolin-6-yl)oxyheptanamidyl)acetic acid;
2-(N-phenyl-7-(2-oxo-1,2,3,5-tetrahydroimidazo[2,1-b]quinazolin-6-yl)oxyheptanamidyl)acetic acid;
2-(N-cyclohexyl-7-(2-oxo-7-chloro-1,2,3,5-tetrahydroimidazo[2,1-b]quinazolin-6-yl)oxyheptanamidyl)acetic acid;
2-(N-cyclohexyl-7-(2-oxo-7-methyl-1,2,3,5-tetrahydroimidazo[2,1-b]quinazolin-6-yl)oxyheptanamidyl)acetic acid;
2-(N-cyclohexyl-7-(2-oxo-9-chloro-1,2,3,5-tetrahydroimidazo[2,1-b]quinazolin-6-yl)oxyheptanamidyl)acetic acid;
2-(N-benzyl-7-(2-oxo-1,2,3,5-tetrahydroimidazo[2,1-b]quinazolin-6-yl)oxyheptanamidyl)acetic acid;
2-(N-cyclopentyl-7-(2-oxo-1,2,3,5-tetrahydroimidazo[2,1-b]quinazolin-6-yl)oxyheptanamidyl)acetic acid;
2-(N-cyclopentylbutyl-7-(2-oxo-1,2,3,5-tetrahydroimidazo[2,1-b]quinazolin-6-yl)oxyheptanamidyl)acetic acid;
2-(N-(4-chlorobenzyl)-7-(2-oxo-1,2,3,5-tetrahydroimidazo[2,1-b]quinazolin-6-yl)oxyheptanamidyl)acetic acid;
2-(N-(4-methoxybenzyl)-7-(2-oxo-1,2,3,5-tetrahydroimidazo[2,1-b]quinazolin-6-yl)oxyheptanamidyl)acetic acid;
2-(N-cyclohexyl-7-(2-oxo-6-methyl-1,2,3,5-tetrahydroimidazo[2,1-b]quinazolin-8-yl)oxyheptanamidyl)acetic acid;
2-(N-cyclohexyl-7-(2-oxo-1,2,3,5-tetrahydroimidazo[2,1-b]quinazolin-8-yl)oxyheptanamidyl)acetic acid;
2-(N-cyclohexylbutyl-7-(2-oxo-1,2,3,5-tetrahydroimidazo[2,1-b]quinazolin-8-yl)oxyheptanamidyl)acetic acid;
2-(N-cyclohexyl-7-(2-oxo-6-chloro-1,2,3,5-tetrahydroimidazo[2,1-b]quinazolin-8-yl)oxyheptanamidyl)acetic acid;
2-(N-phenyl-7-(2-oxo-1,2,3,5-tetrahydroimidazo[2,1-b]quinazolin-8-yl)oxyheptanamidyl)acetic acid;
2-(N-cyclohexyl-7-(2-oxo-7-chloro-1,2,3,5-tetrahydroimidazo[2,1-b]quinazolin-8-yl)oxyheptanamidyl)acetic acid;
2-(N-cyclohexyl-7-(2-oxo-7-methyl-1,2,3,5-tetrahydroimidazo[2,1-b]quinazolin-8-yl)oxyheptanamidyl)acetic acid;
2-(N-benzyl-7-(2-oxo-1,2,3,5-tetrahydroimidazo[2,1-b]quinazolin-8-yl)oxyheptanamidyl)acetic acid;
2-(N-cyclopentyl-7-(2-oxo-1,2,3,5-tetrahydroimidazo[2,1-b]quinazolin-8-yl)oxyheptanamidyl)acetic acid;
2-(N-cyclopentylmethyl-7-(2-oxo-1,2,3,5-tetrahydroimidazo[2,1-b]quinazolin-8-yl)oxyheptanamidyl)acetic acid;
2-(N-cyclopentylbutyl-7-(2-oxo-1,2,3,5-tetrahydroimidazo[2,1-b]quinazolin-8-yl)oxyheptanamidyl)acetic acid;
2-(N-diphenylmethyl-7-(2-oxo-1,2,3,5-tetrahydroimidazo[2,1-b]quinazolin-8-yl)oxyheptanamidyl)acetic acid;

2-(N-phenyl-7-(2-oxo-1,2,3,5-tetra-hydroimidazo[2,1-b]quinazolin-8-yl)oxyheptanamidyl)acetic acid;

2-(N-(4-chlorobenzyl)-7-(2-oxo-1,2,3,5-tetrahydroimidazo[2,1-b]quinazolin-8-yl)oxyheptanamidyl)acetic acid;

2-(N-phenyl-7-(2-oxo-1,2,3,5-tetrahydroimidazo[2,1-b]quinazolin-9-yl)oxyheptanamidyl)acetic acid;

2-(N-cyclohexylbutyl-7-(2-oxo-1,2,3,5-tetrahydroimidazo[2,1-b]quinazolin-9-yl)oxyheptanamidyl)acetic acid;

2-(N-cyclohexyl-7-(2-oxo-1,2,3,5-tetrahydroimidazo[2,1-b]quinazolin-9-yl)oxyheptanamidyl)acetic acid;

2-(N-benzyl-7-(2-oxy-1,2,3,5-tetrahydroimidazo[2,1-b]quinazolin-9-yl)oxyheptanamidyl)acetic acid;

2-(N-cyclopentyl-7-(2-oxy-6-methyl-1,2,3,5-tetrahydroimidazo[2,1-b]quinazolin-9-yl)oxyheptanamidyl)acetic acid;

2-(N-cyclohexyl-2-(2-oxo-1,2,3,5-tetrahydroimidazo[2,1-b]quinazolin-7-yl)oxyacetamidyl)acetic acid;

2-(N-phenyl-2-(2-oxo-1,2,3,5-tetrahydroimidazo[2,1-b]quinazolin-7-yl)oxyacetamidyl)acetic acid;

2-(N-cyclohexylmethyl-2-(2-oxo-5-methyl-1,2,3,5-tetrahydroimidazo[2,1-b]quinazolin-7-yl)oxyacetamidyl)acetic acid;

2-(N-phenyl-2-(2-oxo-3-methyl-1,2,3,5-tetrahydroimidazo[2,1-b]quinazolin-7-yl)oxyacetamidyl)acetic acid;

2-(N-cyclohexyl-2-(2-oxo-6-chloro-1,2,3,5-tetrahydroimidazo[2,1-b]quinazolin-7-yl)oxyacetamidyl)acetic acid;

2-(N-methyl-2-(2-oxo-1,2,3,5-tetrahydroimidazo[2,1-b]quinazolin-7-yl)oxyacetamidyl)acetic acid;

2-(N-hexyl-2-(2-oxo-1,2,3,5-tetrahydroimidazo[2,1-b]quinazolin-7-yl)oxyacetamidyl)acetic acid;

2-(N-cyclohexyl-2-(2-oxo-3-methyl-6-chloro-1,2,3,5-tetrahydroimidazo[2,1-b]quinazolin-7-yl)oxyacetamidyl)acetic acid;

2-(N-cyclopentylbutyl-2-(2-oxo-1,2,3,5-tetrahydroimidazo[2,1-b]quinazolin-7-yl)oxyacetamidyl)acetic acid;

2-(N-cyclohexyl-2-(2-oxo-6-methyl-1,2,3,5-tetrahydroimidazo[2,1-b]quinazolin-7-yl)oxyacetamidyl)acetic acid;

2-(N-cyclopentyl-2-(2-oxo-6-chloro-1,2,3,5-tetrahydroimidazo[2,1-b]quinazolin-7-yl)oxyacetamidyl)acetic acid;

2-(N-phenyl-2-(2-oxo-1,2,3,5-tetrahydroimidazo[2,1-b]quinazolin-6-yl)oxyacetamidyl)acetic acid;

2-(N-cyclohexyl-2-(2-oxo-7-chloro-1,2,3,5-tetrahydroimidazo[2,1-b]quinazolin-6-yl)oxyacetamidyl)acetic acid;

2-(N-benzyl-2-(2-oxo-1,2,3,5-tetrahydroimidazo[2,1-b]quinazolin-6-yl)oxyacetamidyl)acetic acid;

2-(N-cyclohexyl-2-(2-oxo-1,2,3,5-tetrahydroimidazo[2,1-b]quinazolin-8-yl)oxyacetamidyl)acetic acid;

2-(N-cyclohexylbutyl-2-(2-oxo-1,2,3,5-tetrahydroimidazo[2,1-b]quinazolin-8-yl)oxyacetamidyl)acetic acid;

2-(N-phenyl-2-(2-oxo-1,2,3,5-tetrahydroimidazo[2,1-b]quinazolin-8-yl)oxyacetamidyl)acetic acid;

2-(N-cyclopentyl-2-(2-oxo-1,2,3,5-tetrahydroimidazo[2,1-b]quinazolin-8-yl)oxyacetamidyl)acetic acid;

2-(N-cyclopentylmethyl-2-(2-oxo-1,2,3,5-tetrahydroimidazo[2,1-b]quinazolin-8-yl)oxyacetamidyl)acetic acid;

2-(N-cyclopentyl-2-(2-oxo-1,2,3,5-tetrahydroimidazo[2,1-b]quinazolin-9-yl)oxyacetamidyl)acetic acid;

2-(N-phenyl-2-(2-oxo-1,2,3,5-tetrahydroimidazo[2,1-b]quinazolin-9-yl)oxyacetamidyl)acetic acid;

2-(N-cyclohexyl-2-(2-oxo-1,2,3,5-tetrahydroimidazo[2,1-b]quinazolin-9-yl)oxyacetamidyl)acetic acid;

2-(N-methyl-2-(2-oxo-1,2,3,5-tetrahydroimidazo[2,1-b]quinazolin-9-yl)oxyacetamidyl)acetic acid;

2-(N-cyclohexylmethyl-5-(2-oxo-1,2,3,5-tetrahydroimidazo[2,1-b]quinazolin-7-yl)oxypentanamidyl)acetic acid;

2-(N-phenyl-5-(2-oxo-1,2,3,5-tetrahydroimidazo[2,1-b]quinazolin-7-yl)oxypentanamidyl)acetic acid;

2-(N-cyclohexylmethyl-5-(2-oxo-5-methyl-1,2,3,5-tetrahydroimidazo[2,1-b]quinazolin-7-yl)oxypentanamidyl)acetic acid;

2-(N-phenyl-5-(2-oxo-3-methyl-1,2,3,5-tetrahydroimidazo[2,1-b]quinazolin-7-yl)oxypentanamidyl)acetic acid;

2-(N-cyclohexyl-5-(2-oxo-6-chloro-1,2,3,5-tetrahydroimidazo[2,1-b]quinazolin-7-yl)oxypentanamidyl)acetic acid;

2-(N-cyclohexyl-5-(2-oxo-3-methyl-6-chloro-1,2,3,5-tetrahydroimidazo[2,1-b]quinazolin-7-yl)oxypentanamidyl)acetic acid;

2-(N-cyclohexyl-5-(2-oxo-1,2,3,5-tetrahydroimidazo[2,1-b]quinazolin-7-yl)oxypentanamidyl)acetic acid;

2-(N-cyclopentylbutyl-5-(2-oxo-1,2,3,5-tetrahydroimidazo[2,1-b]quinazolin-7-yl)oxypentanamidyl)acetic acid;

2-(N-cyclohexyl-5-(2-oxo-6-methyl-1,2,3,5-tetrahydroimidazo[2,1-b]quinazolin-7-yl)oxypentanamidyl)acetic acid;

2-(N-cyclohexyl-5-(2-oxo-6-chloro-1,2,3,5-tetrahydroimidazo[2,1-b]quinazolin-7-yl)oxypentanamidyl)acetic acid;

2-(N-cyclohexyl-5-(2-oxo-6-methoxy-1,2,3,5-tetrahydroimidazo[2,1-b]quinazolin-7-yl)oxypentanamidyl)acetic acid;

2-(N-benzyl-5-(2-oxo-1,2,3,5-tetrahydroimidazo[2,1-b]quinazolin-7-yl)oxypentanamidyl)acetic acid;

2-(N-cyclohexylbutyl-5-(2-oxo-1,2,3,5-tetrahydroimidazo[2,1-b]quinazolin-7-yl)oxypentanamidyl)acetic acid;

2-(N-cyclopentyl-5-(2-oxo-6-chloro-1,2,3,5-tetrahydroimidazo[2,1-b]quinazolin-7-yl)oxypentanamidyl)acetic acid;

2-(N-diphenylmethyl-5-(2-oxo-1,2,3,5-tetrahydroimidazo[2,1-b]quinazolin-7-yl)oxypentanamidyl)acetic acid;

2-(N-n-hexyl-5-(2-oxo-1,2,3,5-tetrahydroimidazo[2,1-b]quinazolin-7-yl)oxypentanamidyl)acetic acid;

2-(N-phenyl-5-(2-oxo-1,2,3,5-tetrahydroimidazo[2,1-b]quinazolin-7-yl)oxypentanamidyl)acetic acid;

2-(N-benzyl-5-(2-oxo-1,2,3,5-tetrahydroimidazo[2,1-b]quinazolin-7-yl)oxypentanamidyl)acetic acid;

2-(N-(4-chlorobenzyl)-5-(2-oxo-1,2,3,5-tetrahydroimidazo[2,1-b]quinazolin-7-yl)oxypentanamidyl)acetic acid;

2-(N-(4-methoxybenzyl)-5-(2-oxo-1,2,3,5-tetrahydroimidazo[2,1-b]quinazolin-7-yl)oxypentanamidyl)acetic acid;

2-(N-cyclohexylbutyl-5-(2-oxo-1,2,3,5-tetrahydroimidazo[2,1-b]quinazolin-6-yl)oxypentanamidyl)acetic acid;
2-(N-cyclohexyl-5-(2-oxo-7-chloro-1,2,3,5-tetrahydroimidazo[2,1-b]quinazolin-6-yl)oxypentanamidyl)acetic acid;
2-(N-cyclohexyl-5-(2-oxo-7-methyl-1,2,3,5-tetrahydroimidazo[2,1-b]quinazolin-6-yl)oxypentanamidyl)acetic acid;
2-(N-cyclohexyl-5-(2-oxo-9-chloro-1,2,3,5-tetrahydroimidazo[2,1-b]quinazolin-6-yl)oxypentanamidyl)acetic acid;
2-(N-cyclopentyl-5-(2-oxo-1,2,3,5-tetrahydroimidazo[2,1-b]quinazolin-6-yl)oxypentanamidyl)acetic acid;
2-(N-(4-chlorobenzyl)-5-(2-oxo-1,2,3,5-tetrahydroimidazo[2,1-b]quinazolin-6-yl)oxypentanamidyl)acetic acid;
2-(N-(4-methoxybenzyl)-5-(2-oxo-1,2,3,5-tetrahydroimidazo[2,1-b]quinazolin-6-yl)oxypentanamidyl)acetic acid;
2-(N-cyclohexyl-5-(2-oxo-6-methyl-1,2,3,5-tetrahydroimidazo[2,1-b]quinazolin-8-yl)oxypentanamidyl)acetic acid;
2-(N-cyclohexyl-5-(2-oxo-6-methoxy-1,2,3,5-tetrahydroimidazo[2,1-b]quinazolin-8-yl)oxypentanamidyl)acetic acid;
2-(N-cyclohexylbutyl-5-(2-oxo-1,2,3,5-tetrahydroimidazo[2,1-b]quinazolin-8-yl)oxypentanamidyl)acetic acid;
2-(N-cyclohexyl-5-(2-oxo-6-chloro-1,2,3,5-tetrahydroimidazo[2,1-b]quinazolin-8-yl)oxypentanamidyl)acetic acid;
2-(N-phenyl-5-(2-oxo-1,2,3,5-tetrahydroimidazo[2,1-b]quinazolin-8-yl)oxypentanamidyl)acetic acid;
2-(N-cyclohexyl-5-(2-oxo-7-chloro-1,2,3,5-tetrahydroimidazo[2,1-b]quinazolin-8-yl)oxypentanamidyl)acetic acid;
2-(N-cyclohexyl-5-(2-oxo-7-methyl-1,2,3,5-tetrahydroimidazo[2,1-b]quinazolin-8-yl)oxypentanamidyl)acetic acid;
2-(N-benzyl-5-(2-oxo-1,2,3,5-tetrahydroimidazo[2,1-b]quinazolin-8-yl)oxypentanamidyl)acetic acid;
2-(N-cyclopentyl-5-(2-oxo-1,2,3,5-tetrahydroimidazo[2,1-b]quinazolin-8-yl)oxypentanamidyl)acetic acid;
2-(N-cyclopentylmethyl-5-(2-oxo-1,2,3,5-tetrahydroimidazo[2,1-b]quinazolin-8-yl)oxypentanamidyl)acetic acid;
2-(N-cyclopentylbutyl-5-(2-oxo-1,2,3,5-tetrahydroimidazo[2,1-b]quinazolin-8-yl)oxypentanamidyl)acetic acid;
2-(N-diphenylmethyl-5-(2-oxo-1,2,3,5-tetrahydroimidazo[2,1-b]quinazolin-8-yl)oxypentanamidyl)acetic acid;
2-(N-phenyl-5-(2-oxo-1,2,3,5-tetrahydroimidazo[2,1-b]quinazolin-9-yl)oxypentanamidyl)acetic acid;
2-(N-cyclohexylbutyl-5-(2-oxo-1,2,3,5-tetrahydroimidazo[2,1-b]quinazolin-9-yl)oxypentanamidyl)acetic acid;
2-(N-cyclohexyl-5-(2-oxo-1,2,3,5-tetrahydroimidazo[2,1-b]quinazolin-9-yl)oxypentanamidyl)acetic acid;
2-(N-methyl-5-(2-oxo-1,2,3,5-tetrahydroimidazo[2,1-b]quinazolin-9-yl)oxypentanamidyl)acetic acid;
2-(N-benzyl-5-(2-oxo-1,2,3,5-tetrahydroimidazo[2,1-b]quinazolin-9-yl)oxypentanamidyl)acetic acid;
2-(N-cyclopentyl-5-(2-oxo-6-methyl-1,2,3,5-tetrahydroimidazo[2,1-b]quinazolin-9-yl)oxypentanamidyl)acetic acid;
2-(N-cyclohexyl-6-(2-oxo-1,2,3,5-tetrahydroimidazo[2,1-b]quinazolin-7-yl)oxyhexanamidyl)acetic acid;
2-(N-cyclohexylmethyl-6-(2-oxo-1,2,3,5-tetrahydroimidazo[2,1-b]quinazolin-7-yl)oxyhexanamidyl)acetic acid;
2-(N-phenyl-6-(2-oxo-1,2,3,5-tetrahydroimidazo[2,1-b]quinazolin-7-yl)oxyhexanamidyl)acetic acid;
2-(N-methyl-6-(2-oxo-1,2,3,5-tetrahydroimidazo[2,1-b]quinazolin-7-yl)oxyhexanamidyl)acetic acid;
2-(N-phenyl-6-(2-oxo-3-methyl-1,2,3,5-tetrahydroimidazo[2,1-b]quinazolin-7-yl)oxyhexanamidyl)acetic acid;
2-(N-cyclohexyl-6-(2-oxo-6-chloro-1,2,3,5-tetrahydroimidazo[2,1-b]quinazolin-7-yl)oxyhexanamidyl)acetic acid;
2-(N-cyclohexyl-6-(2-oxo-3-methyl-6-chloro-1,2,3,5-tetrahydroimidazo[2,1-b]quinazolin-7-yl)oxyhexanamidyl)acetic acid;
2-(N-cyclohexylbutyl-6-(2-oxo-1,2,3,5-tetrahydroimidazo[2,1-b]quinazolin-7-yl)oxyhexanamidyl)acetic acid;
2-(N-cyclohexyl-6-(2-oxo-6-methyl-1,2,3,5-tetrahydroimidazo[2,1-b]quinazolin-7-yl)oxyhexanamidyl)acetic acid;
2-(N-cyclohexyl-6-(2-oxo-6-chloro-1,2,3,5-tetrahydroimidazo[2,1-b]quinazolin-7-yl)oxyhexanamidyl)acetic acid;
2-(N-cyclohexyl-6-(2-oxo-6-methoxy-1,2,3,5-tetrahydroimidazo[2,1-b]quinazolin-7-yl)oxyhexanamidyl)acetic acid;
2-(N-benzyl-6-(2-oxo-1,2,3,5-tetrahydroimidazo[2,1-b]quinazolin-7-yl)oxyhexanamidyl)acetic acid;
2-(N-cyclohexyl-6-(2-oxo-6-methoxy-1,2,3,5-tetrahydroimidazo[2,1-b]quinazolin-7-yl)oxyhexanamidyl)acetic acid;
2-(N-diphenylmethyl-6-(2-oxo-1,2,3,5-tetrahydroimidazo[2,1-b]quinazolin-7-yl)oxyhexanamidyl)acetic acid;
2-(N-n-hexyl-6-(2-oxo-1,2,3,5-tetrahydroimidazo[2,1-b]quinazolin-7-yl)oxyhexanamidyl)acetic acid;
2-(N-phenyl-6-(2-oxo-1,2,3,5-tetrahydroimidazo[2,1-b]quinazolin-7-yl)oxyhexanamidyl)acetic acid;
2-(N-(4-chlorobenzyl)-6-(2-oxo-1,2,3,5-tetrahydroimidazo[2,1-b]quinazolin-7-yl)oxyhexanamidyl)acetic acid;
2-(N-(4-methoxybenzyl)-6-(2-oxo-1,2,3,5-tetrahydroimidazo[2,1-b]quinazolin-7-yl)oxyhexanamidyl)acetic acid;
2-(N-cyclohexylbutyl-6-(2-oxo-1,2,3,5-tetrahydroimidazo[2,1-b]quinazolin-6-yl)oxyhexanamidyl)acetic acid;
2-(N-phenyl-6-(2-oxo-1,2,3,5-tetrahydroimidazo[2,1-b]quinazolin-6-yl)oxyhexanamidyl)acetic acid;
2-(N-cyclohexyl-4-(2-oxo-7-chloro-1,2,3,5-tetrahydroimidazo[2,1-b]quinazolin-6-yl)oxyhexanamidyl)acetic acid;
2-(N-cyclohexyl-4-(2-oxo-7-methyl-1,2,3,5-tetrahydroimidazo[2,1-b]quinazolin-6-yl)oxyhexanamidyl)acetic acid;
2-(N-cyclohexyl-6-(2-oxo-9-chloro-1,2,3,5-tetrahydroimidazo[2,1-b]quinazolin-6-yl)oxyhexanamidyl)acetic acid;
2-(N-benzyl-6-(2-oxo-1,2,3,5-tetrahydroimidazo[2,1-b]quinazolin-6-yl)oxyhexanamidyl)acetic acid;

2-(N-cyclopentyl-6-(2-oxo-1,2,3,5-tetrahydroimidazo[2,1-b]quinazolin-6-yl)oxyhexanamidyl)acetic acid;
2-(N-cyclopentylbutyl-6-(2-oxo-1,2,3,5-tetrahydroimidazo[2,1-b]quinazolin-6-yl)oxyhexanamidyl)acetic acid;
2-(N-4-chlorobenzyl-6-(2-oxo-1,2,3,5-tetrahydroimidazo[2,1-b]quinazolin-6-yl)oxyhexanamidyl)acetic acid;
2-(N-4-methoxybenzyl-6-(2-oxo-1,2,3,5-tetrahydroimidazo[2,1-b]quinazolin-6-yl)oxyhexanamidyl)acetic acid;
2-(N-cyclohexyl-6-(2-oxo-6-methyl-1,2,3,5-tetrahydroimidazo[2,1-b]quinazolin-8-yl)oxyhexanamidyl)acetic acid;
2-(N-cyclohexyl-6-(2-oxo-6-methoxy-1,2,3,5-tetrahydroimidazo[2,1-b]quinazolin-8-yl)oxyhexanamidyl)acetic acid;
2-(N-cyclohexylbutyl-6-(2-oxo-1,2,3,5-tetrahydroimidazo[2,1-b]quinazolin-8-yl)oxyhexanamidyl)acetic acid;
2-(N-cyclohexyl-6-(2-oxo-6-chloro-1,2,3,5-tetrahydroimidazo[2,1-b]quinazolin-8-yl)oxyhexanamidyl)acetic acid;
2-(N-phenyl-6-(2-oxo-1,2,3,5-tetrahydroimidazo[2,1-b]quinazolin-8-yl)oxyhexanamidyl)acetic acid;
2-(N-cyclohexyl-6-(2-oxo-7-chloro-1,2,3,5-tetrahydroimidazo[2,1-b]quinazolin-8-yl)oxyhexanamidyl)acetic acid;
2-(N-cyclohexyl-6-(2-oxo-7-methyl-1,2,3,5-tetrahydroimidazo[2,1-b]quinazolin-8-yl)oxyhexanamidyl)acetic acid;
2-(N-benzyl-6-(2-oxo-1,2,3,5-tetrahydroimidazo[2,1-b]quinazolin-8-yl)oxyhexanamidyl)acetic acid;
2-(N-cyclopentyl-6-(2-oxo-1,2,3,5-tetrahydroimidazo[2,1-b]quinazolin-8-yl)oxyhexanamidyl)acetic acid;
2-(N-cyclopentylmethyl-6-(2-oxo-1,2,3,5-tetrahydroimidazo[2,1-b]quinazolin-8-yl)oxyhexanamidyl)acetic acid;
2-(N-cyclopentylbutyl-6-(2-oxo-1,2,3,5-tetrahydroimidazo[2,1-b]quinazolin-8-yl)oxyhexanamidyl)acetic acid;
2-(N-diphenylmethyl-6-(2-oxo-1,2,3,5-tetrahydroimidazo[2,1-b]quinazolin-8-yl)oxyhexanamidyl)acetic acid;
2-(N-(4-chlorobenzyl)-6-(2-oxo-1,2,3,5-tetrahydroimidazo[2,1-b]quinazolin-8-yl)oxyhexanamidyl)acetic acid;
2-(N-cyclohexyl-6-(2-oxo-1,2,3,5-tetrahydroimidazo[2,1-b]quinazolin-9-yl)oxyhexanamidyl)acetic acid;
2-(N-cyclopentyl-6-(2-oxo-1,2,3,5-tetrahydroimidazo[2,1-b]quinazolin-9-yl)oxyhexanamidyl)acetic acid;
2-(N-phenyl-6-(2-oxo-1,2,3,5-tetrahydroimidazo[2,1-b]quinazolin-9-yl)oxyhexanamidyl)acetic acid;
2-(N-cyclohexylbutyl-6-(2-oxo-1,2,3,5-tetrahydroimidazo[2,1-b]quinazolin-9-yl)oxyhexanamidyl)acetic acid;
2-(N-benzyl-6-(2-oxy-1,2,3,5-tetrahydroimidazo[2,1-b]quinazolin-9-yl)oxyhexanamidyl)acetic acid; and
2-(N-cyclopentyl-6-(2-oxo-6-methyl-1,2,3,5-tetrahydroimidazo[2,1-b]quinazolin-9-yl)oxyhexanamidyl)acetic acid.

EXAMPLE 3

Methyl 2-(N-cyclohexyl-4-(2-oxo-3-D-hydroxymethyl-1,2,3,5-tetrahydroimidazo[2,1-b]quinazolin-7-yl)oxybutyramidyl)acetate To a solution of methyl 2-(N-cyclohexyl-4-(3-formyl-4-nitrophenyl)oxybutyramid-1-yl)acetate (25 mmol), D-serine methyl ester hydrochloride (7.0 g, 50 mmol) and 3 Å molecular sieves (5.0 g) in methanol (75 ml) was added D-serine methyl ester (20.6 g, 200 mmol). After allowing the solution to stir for 5 minutes at room temperature, sodium cyanoborohydride (0.95 g, 15 mmol) was added in one amount. The reaction mixture was allowed to stir at room temperature for 3–4 hours. The reaction solution was then filtered to remove precipitated solids and molecular sieves, and the methanol was removed by evaporation. The residue was dissolved in ethyl acetate (300 ml) and was washed with saturated sodium bicarbonate ($2 \times 100$ ml) and brine ($2 \times 100$ ml). The organic extract was dried, filtered and evaporated to give a thick syrup. The thick syrupy residue was dissolved in absolute ethanol (100 ml) and hydrogenated over 10% Pd-C (1.0 g) until uptake of hydrogen ceased, approximately 4 hours. The catalyst was removed by filtration through a pad of Celite, and pad was washed clean with absolute ethanol (50 ml). The combined filtrates were treated with cyanogen bromide (3.20 g, 30 mmol), and the resulting solution maintained at a reflux for 16 hours. Upon cooling, the ethanol was removed, and the residue was dissolved in ethanol (100 ml) and treated with ammonium hydroxide (25 ml) and stirred for 2 hours at room temperature. The product was precipitated from this mixture and further purified by filtration and a water wash, dried, yielding methyl 2-(N-cyclohexyl-4-(2-oxo-3-D-hydroxymethyl-1,2,3,5-tetrahydroimidazo[2,1-b]quinazolin-7-yl)oxybutyramid-1-yl)acetate.

Proceeding in a like manner but substituting D-serine methyl ester with other appropriate optically active α-aminocarboxylic acid esters, there may be prepared the following exemplary optical isomers of Formula I:

methyl 2-(N-cyclohexyl-4-(2-oxo-3-L-hydroxymethyl-1,2,3,5-tetrahydroimidazo[2,1-b]quinazolin-7-yl)oxybutyramidyl)acetate;
methyl 2-(N-cyclohexyl-4-(2-oxo-3-L-methyl-1,2,3,5-tetrahydroimidazo[2,1-b]quinazolin-7-yl)oxybutyramidyl)acetate;
methyl 2-(N-cyclohexyl-4-(2-oxo-3-D-methyl-1,2,3,5-tetrahydroimidazo[2,1-b]quinazolin-7-yl)oxybutyramidyl)acetate;
methyl 2-(N-cyclohexyl-4-(2-oxo-3-D-ethyl-1,2,3,5-tetrahydroimidazo[2,1-b]quinazolin-7-yl)oxybutyramidyl)acetate;
methyl 2-(N-cyclohexyl-4-(2-oxo-3-L-ethyl-1,2,3,5-tetrahydroimidazo[2,1-b]quinazolin-7-yl)oxybutyramidyl)acetate;
methyl 2-(N-cyclohexyl-4-(2-oxo-3-D-(1-hydroxyethyl)-1,2,3,5-tetrahydroimidazo[2,1-b]quinazolin-7-yl)oxybutyramidyl)acetate;
methyl 2-(N-cyclohexyl-4-(2-oxo-3-L-(1-hydroxyethyl)-1,2,3,5-tetrahydroimidazo[2,1-b]quinazolin-7-yl)oxybutyramidyl)acetate;
methyl 2-(N-cyclohexyl-4-(2-oxo-3-D-isopropyl-1,2,3,5-tetrahydroimidazo[2,1-b]quinazolin-7-yl)oxybutyramidyl)acetate;

methyl 2-(N-cyclohexyl-4-(2-oxo-3-L-isopropyl-1,2,3,5-tetrahydroimidazo[2,1-b]quinazolin-7-yl)oxybutyramidyl)acetate;

methyl 2-(N-cyclohexyl-4-(2-oxo-3-D-benzyl-1,2,3,5-tetrahydroimidazo[2,1-b]quinazolin-7-yl)oxybutyramidyl)acetate;

methyl 2-(N-cyclohexyl-4-(2-oxo-3-L-benzyl-1,2,3,5-tetrahydroimidazo[2,1-b]quinazolin-7-yl)oxybutyramidyl)acetate;

methyl 2-(N-cyclohexyl-4-(2-oxo-3-D-phenyl-1,2,3,5-tetrahydroimidazo[2,1-b]quinazolin-7-yl)oxybutyramidyl)acetate;

methyl 2-(N-cyclohexyl-4-(2-oxo-3-L-phenyl-1,2,3,5-tetrahydroimidazo[2,1-b]quinazolin-7-yl)oxybutyramidyl)acetate;

methyl 2-(N-cyclohexyl-4-(2-oxo-3-D-acetoxymethyl-1,2,3,5-tetrahydroimidazo[2,1-b]quinazolin-7-yl)oxybutyramidyl)acetate;

methyl 2-(N-cyclohexyl-4-(2-oxo-3-L-acetoxymethyl-1,2,3,5-tetrahydroimidazo[2,1-b]quinazolin-7-yl)oxybutyramidyl)acetate;

methyl 2-(N-cyclohexyl-4-(2-oxo-3-D-carbamoylmethyl-1,2,3,5-tetrahydroimidazo[2,1-b]quinazolin-7-yl)oxybutyramidyl)acetate; and methyl 2-(N-cyclohexyl-4-(2-oxo-3-L-carbamoylmethyl-1,2,3,5-tetrahydroimidazo[2,1-b]quinazolin-7-yl)oxybutyramidyl)acetate.

These compounds are converted to their acetic acid analogues by the saponification procedure set out in Example 2 above.

EXAMPLE 3

Methyl 2-(N-cyclohexyl-4-(2,5-dioxo-1,2,3,5-tetrahydroimidazo[2,1-b]quinazolin-7-yl)oxybutyramidyl)acetate To a suspension of methyl 5-(4-(N-cyclohexyl-N-methylacetoxy)butyramidyl)oxyanthranilic acid (0.05 g, 1.5 mmol) in ethanol (10 ml) was added an ethanolic solution of freshly prepared 2-methylthiohydantoin (3.4 mmol). The dark mixture was heated and maintained at reflux for 3 hours. The reaction mixture was then cooled, diluted with water and triturated to give methyl 2-(N-cyclohexyl-4-(2,5-dioxo-1,2,3,5-tetrahydroimidazo[2,1-b]quinazolin-7-yl)oxybutyramidyl)acetate.

This and other analogous compounds are then converted to the free acid by the procedure set out in Example 2.

EXAMPLE 5

Methyl 2-(N-cyclohexyl-4-(2-oxo-1,2,3,5-tetrahydroimidazo[2,1-b]quinazolin-7-yl)oxybutyramidyl)acetate To a solution of 4-(2-oxo-1,2,3,5-tetrahydroimadazo[2,1-b]quinazolin-7-yl)oxybutyric acid (3.44 g) and 1-hydroxybenzotriazole (1.5 g) in 25 ml dry dimethylformamide was added diisopropylcarbodiimide (1.39 g). After one hour at room temperature, a solution of methyl N-cyclohexylglycinate (1.56 ml) and 1.32 ml of N-methylmorpholine in 10 ml of dry dimethylformamide was added. The resulting solution was stirred overnight at room temperature and was then diluted with water. The resulting precipitate was collected and dried over phosphorous pentoxide to give methyl 2-(N-cyclohexyl-4-(2-oxo-1,2,3,4-tetrahydroimadazo[2,1-b]quinazolin-7-yl)oxybutyramid-1-yl)acetate.

Proceeding in a similar manner, all oxyalkyl acids prepared as per Preparation 13 are converted to their corresponding ester.

These esters are then converted to the free acid by the procedure set out in Example 2.

EXAMPLE 6

Methyl 2-N-cyclohexyl-4-(2-oxo-1,2,3,5-tetrahydroimidazo[2,1-b]quinazolin-7-yl)oxybutyramidyl)acetate Into a solution of the ethyl ester (3.2 g, 10 mmol) prepared in Preparation 12 and tetra-N-butylammonium bromide (6.44 g, 20 mmol) in DMF (100 ml) was added aqueous KOH (1.5 g in 5 ml $H_2O$), stirred overnight at room temperature. Molecular sieves (3 Å, 25 g) were added, and the mixture was left to stand 3 days. Methyl N-cyclohexylglycinate (2.6 ml, 20 mmol) and bis(o-nitrophenyl)phenylphosphonate (10 g, 25 mmol) were added, and the mixture was shaken for 24 hours. The mixture was filtered through Celite, and the DMF was evaporated at high vacuum. The residue was triturated with 5% aqueous ammonium hydroxide and ethanol (1:1) to give a precipitate, collected by filtration, washed with ethanol and dried to give methyl 2-N-cyclohexyl-4-(2-oxo-1,2,3,5-tetrahydroimidazo[2,1-b]quinazolin-7-yl)oxybutyramidyl)acetate.

EXAMPLE 7

Methyl 2-N-cyclohexyl-4-(2-oxo-1,2,3,5-tetrahydroimidazo[2,1-b]quinazolin-7-yl)oxybutyramidyl)acetate The compounds of Formula I wherein $R_4$ is hydrogen are converted to those wherein $R_4$ is alkyl of 1 to 6 carbon atoms, benzyl or hydroxy lower alkyl by the following procedure.

To a solution of methyl 2-(N-cyclohexyl-4-(2-oxo-1,2,3,5-tetrahydroimidazo[2,1-b]quinazolin-7-yl)oxybutyramidyl)acetate in dry dimethylformamide was added sodium hydride (1.05 equivalents). The mixture was stirred at 60° C. for 30 minutes to give a homogeneous solution. 1-Bromobutane (1.1 equivalents) was added via a syringe after which the mixture was evaporated. The residue was dissolved in ethyl acetate and washed with saturated brine, dried and filtered. Evaporation of the solvent afforded methyl 2-(N-cyclohexyl-4-(1-butyl-2-oxo-1,2,3,5-tetrahydroimidazo[2,1-b]quinazolin-7-yl)oxybutyramidyl)acetate.

EXAMPLE 8

Conversion of Free Base to Salt

A two-fold stoichiometric excess of 3% hydrogen chloride in methanol is added to a solution of 1.0 g. of methyl 2-(N-cyclohexyl-4-(2-oxo-1,2,3,5-tetrahydroimidazo[2,1-b]quinazolin-7-yl)oxybutyramidyl)acetate in 20 ml methanol. Diethyl ether is added until precipitation is complete. The product is filtered, washed with ether, air dried and recrystallized to give methyl 2-(N-cyclohexyl-4-(2-oxo-1,2,3,5-tetrahydroimidazo[2,1-b]quinazolin-7-yl)oxybutyramidyl)acetate hydrochloride.

EXAMPLE 9

Conversion of Salt to Free Base 1.0 g of methyl 2-(N-cyclohexyl-4-(2-oxo-1,2,3,5-tetrahydroimidazo[2,1-b]quinazolin-7-yl)oxybutyramidyl)acetate HCl suspended in 50 ml of ether is stirred with one equivalent of dilute aqueous potassium carbonate solution until the salt is completely dissolved. The organic layer is then separated, washed twice with water, dried over magnesium sulfate and evaporated to yield methyl 2-(N-cyclohexyl-4-(2-oxo-1,2,3,5-tetrahydroimidazo[2,1-b]quinazolin-7-yl)oxybutyramidyl)acetate as the free base.

EXAMPLE 10

Compounds of the present invention, either the free base or a pharmaceutically acceptable salt, may be orally administered to a subject as a tablet. While the active ingredient may comprise anywhere between about 1 and about 99 percent of the formulation, that percentage preferably will be an amount which will cause to be delivered to the subject the active ingredient in an amount of between 20 mg and 100 mg per tablet. Following is a representative tablet formulation in which the active ingredient is methyl N-cyclohexyl-4-(2-oxo-1,2,3,5-tetrahydroimidazo[2,1-b]quinazolin-7-yl)oxybutyramidyl)acetate. However, the formulation profile given below may be used to formulate a tablet for any of the compounds represented by Formula I.

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 11

An alternative oral dosage form is hard shell gelatin capsules filled with a powder containing the active ingredient in the desired amount. Using the active ingredient mentioned in Example 6 above, the acid addition salts, or any other compound according to Formula I there may be prepared an exemplary hard shell gelatin capsule formulation using the following ingredients

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 12

Alternatively, compounds of the present invention may be prepared as a suspension for oral administration. Any of the compounds of Formula I, either in freelance form or as the acid addition salt, may be used in this formulation.

An oral suspension is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 13

Cyclic AMP phosphodiesterase activity and inhibition of platelet aggregation were determined as follows.

Cyclic AMP Phosphodiesterase Assay

The inhibition of cyclic AMP phosphodiesterase activity by the subject compounds was assayed by the method of Filburn and Karn, *Analyt. Biochem.*, 52: 505–516 (1973), using 1 μM cyclic AMP as the substrate. Human platelet cyclic AMP phosphodiesterase was obtained from human donors. Platelets were isolated and washed by centrifugation, the membranes ruptured by a sequential freeze-thaw procedure and hypotonic lysis and the soluble enzyme isolated by high speed centrifugation. The enzyme was stored in aliquots at −20° C.

Platelet Aggregation

Blood was collected into evacuated tubes containing sodium citrate (30 mM). Platelet rich plasma was collected after centrifugation. Aggregation was followed by a turbidimetric procedure described by G. V. R. Born, *J. Physiol., Lond.*, 162: 67P–68P (1962).

Inhibition of cyclic AMP phosphodiesterase data (relative to theophylline) are presented in Table I below. This table contains the $IC_{50}$ values for human platelet phosphodiesterase and $IC_{25}$ values for rat heart phosphodiesterase.

TABLE I

INHIBITION OF CYCLIC AMP PHOSPHODIESTERASE IN HUMAN PLATELETS AND ANIMAL HEART

| Compound[c] | Human Platelet $IC_{50}$ [nM] | Heart $IC_{25}$ [nM] | Relative Potency[c] |
| --- | --- | --- | --- |
| methyl 2-(N—cyclohexyl-4-(2-oxo-(1,2,3,5-tetrahydroimidazo[2,1-b]-quinazolin-7-yl)oxybutyramidyl)-yl)acetate | 2.0 | 10.0[a] | 135,000 |
| 2-(N—cyclohexyl-4-(2-oxo-1,2,3,5-tetrahydroimidazo-[2,1-b]-quinazolin-7-yl)-oxybutyramidyl)-acetic acid | 5.0 | 100[b] | 54,000 |
| 2-(N—cyclohexyl-4-(2-oxo-1,2,3,5-tetrahydroimidazo-[2,1-b]-quinazolin-7-yl)-oxybutyramidyl)-acetamide | 11.0 | 100[a] | 24,500 |

[a]Soluble dog heart PDE
[b]Soluble rat heart PDE
[c]Potency relative to theophylline which is assigned a value of 1 on human platelet phosphodiesterase.

EXAMPLE 14

Inotropic Activity of the Compounds of the Present Invention

Mongrel dogs were anesthetized intravenously with 35 mg/kg sodium pentobarbital and supplemented as needed. Blood pressure was measured with a Statham pressure transducer via a cannula inserted from a femoral artery into the abdominal aorta. Heart rate was recorded by a cardiotachometer from a lead II electrocardiogram. Right ventricular contractile force was recorded from a Walton-Brodie strain gauge sutured to the right ventricle following a midsternal thoracotomy. A Harvard respirator was used to ventilate the dogs with room air through an endotracheal tube. Each dog was bilaterally vagotomized. Following a midline laparotomy, a cannula was sutured into the duodenum for intraduodenal administration of test compound. A femoral vein was cannulated for administration of isoproterenol. All data were recorded on a Beckman R611 Dynograph.

To assess the responsiveness of each dog, isoproterenol was given intravenously at half-log interval doses from 0.007 to 6.67 µg/kg. The test compound was then administered intravenously at 1 mg/kg.

The test results are summarized in the following table:

TABLE II

| Compound | Dose (mg/kg) | Peak Effects as % of Max. Isoproterenol | | |
|---|---|---|---|---|
| | | Rt. Ventricular Contractile Force | Heart Rate | Blood Pressure |
| 2-(N—cyclohexyl-4-(2-oxo-1,2,3,5-tetra-hydroimidazo-[2,1-b]-quinazolin-7-yl)-oxybutyramidyl)-acetic acid[a] | 1 (i.v.)[b] | 33 | 30 | 32 |

[a]Suspended in carboxymethylcellulose.
[b]i.v. = intravenous administration.

EXAMPLE 15

Antimetastatic activity against Lewis Lung Carcinoma (Spontaneous Metastases)

Mice (female, C57B1/6, 16–18 g) were inoculated subcutaneously between the inguinal and axillary areas with 0.2 ml of a freshly prepared tumor brei. Control mice were treated with vehicle. Other mice were treated orally with test compound in suspension in 0.5% carboxymethylcellulose (CMC). Treatments were initiated one day after tumor implanation, and continued every other day throughout the experiment. 20 to 21 days after implantation of the tumor, mice were sacrificed, the primary tumor was weighed, and the number of lung metastases was determined by counting under a dissecting microscope. The results are shown in Table III.

TABLE III

| Treatment | Number of Pulmonary Metastases | |
|---|---|---|
| | Median | Range |
| Control | 5 | 0–29 |
| 2-(N—cyclohexyl-4-(2-oxo 1,2,3,5-tetrahydroimidazo-[2,1-b]quinazolin-7-yl)-oxybutyramidyl)acetic acid | 0* | 0–11 |

TABLE III-continued

| Treatment | Number of Pulmonary Metastases | |
|---|---|---|
| | Median | Range |
| (5 mg/kg) | | |

*$p < 0.05$

EXAMPLE 16

In the tests reported above, no toxic effects were observed.

What is claimed is:

1. A compound according to the formula

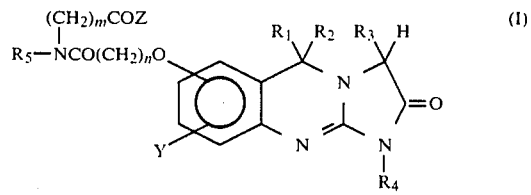

, its optical isomers, or a pharmaceutically acceptable salt thereof wherein:

m and n are integers of 1 to 6;

$R_1$ is hydrogen or alkyl of 1 to 4 carbons;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbon atoms, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_6$, halo, —NH$_2$, —N(R$_6$)$_2$, —NHCOR$_6$, —COOH, or —COO(R$_6$) group wherein R$_6$ is lower alkyl; phenyl or phenyl lower alkyl wherein phenyl is unsubstituted or substituted with 1 or more lower alkyl, halo or lower alkoxy groups or an —NH$_2$, —N(R$_6$)$_2$, —NHCOR$_6$, —COOH, or —COOR$_6$ group wherein R$_6$ is lower alkyl;

Y is hydrogen, alkyl of 1 to 4 carbon atoms, halo or lower alkoxy; and

Z is —OR$_7$ or —NR$_7$R$_8$ wherein R$_7$ and R$_8$ are independently hydrogen or lower alkyl;

or a pharmaceutically acceptable salt thereof.

2. A compound according to claim 1 wherein Z is —OR$_7$ wherein R$_7$ is lower alkyl.

3. A compound of claim 2 wherein $R_1$, $R_2$ and $R_3$ are hydrogen, $R_4$ is hydrogen or methyl, m is 1–3 and n is 3 or 4.

4. A compound according to claim 3 wherein $R_4$ is hydrogen, m is 1, and $R_5$ is alkyl of 1 to 6 carbon atoms, cycloalkyl of 3 to 8 carbon atoms or cycloalkyl lower alkyl of 4 to 12 carbon atoms.

5. A compound according to claim 4 wherein n is 3 and $R_5$ is alkyl of 1 to 6 carbon atoms or cycloalkyl of 3 to 8 carbon atoms.

6. The compound according to claim 5 which is methyl-2-(N-cyclohexyl-4-(2-oxo-1,2,3,5-tetrahydroimidazo[2,1-b]quinazolin-7-yl)oxybutyramidyl)acetate or a pharmaceutically acceptable salt thereof.

7. A compound according to claim 1 wherein Z is —$OR_7$ wherein $R_7$ is hydrogen.

8. A compound of claim 7 wherein $R_1$, $R_2$ and $R_3$ are hydrogen, $R_4$ is hydrogen or methyl, m is 1-3 and n is 3 or 4.

9. A compound according to claim 8 wherein $R_4$ is hydrogen, m is 1, and $R_5$ is alkyl of 1 to 6 carbon atoms, cycloalkyl of 3 to 8 carbon atoms or cycloalkyl lower alkyl of 4 to 12 carbon atoms.

10. A compound according to claim 9 wherein n is 3 and $R_5$ is alkyl of 1 to 6 carbon atoms or cycloalkyl of 3 to 8 carbon atoms.

11. A compound according to claim 10 which is 2-(N-cyclohexyl)-4-(2-oxo-1,2,3,5-tetrahydroimidazo[2,1-b]quinazolin-7-yl)oxybutyramidyl)acetic acid or a pharmaceutically acceptable salt thereof.

12. A compound according to claim 1 wherein Z is —$NR_8R_7$ wherein $R_7$ and $R_8$ are hydrogen.

13. A compound of claim 12 wherein $R_1$, $R_2$ and $R_3$ are hydrogen, $R_4$ is hydrogen or methyl, m is 1-3 and n is 3 or 4.

14. A compound according to claim 13 wherein $R_4$ is hydrogen, m is 1, n is 3 or 4 and $R_5$ is alkyl of 1 to 6 carbon atoms, cycloalkyl of 3 to 8 carbon atoms or cycloalkyl lower alkyl of 4 to 12 carbon atoms.

15. A compound according to claim 14 wherein n is 3 and $R_5$ is alkyl of 1 to 6 carbon atoms or cycloalkyl of 3 to 8 carbon atoms.

16. The compound according to claim 15 which is 2-(N-cyclohexyl-4-(2-oxo-1,2,3,5-tetrahydroimidazo[2,1-b]quinazolin-7-yl)oxybutyramidyl)acetamide or a pharmaceutically acceptable salt thereof.

17. A pharmaceutical composition comprising a pharmaceutically acceptable excipient and a compound of the formula

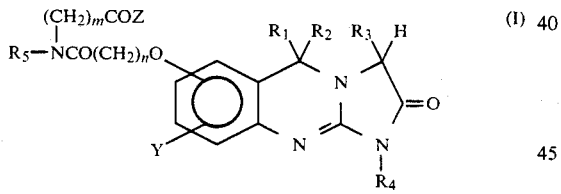

its optical isomers, or a pharmaceutically acceptable salt thereof wherein:

m and n are integers of 1 to 6;

$R_1$ is hydrogen or alkyl of 1 to 4 carbons;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbons, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —$OCOR_6$, halo, —$NH_2$, —$N(R_6)_2$, —$NHCOR_6$, —COOH, or —$COO(R_6)$ group wherein $R_6$ is lower alkyl; phenyl or phenyl lower alkyl wherein phenyl is unsubstituted or substituted with 1 or more lower alkyl, halo or lower alkoxy groups or an —$NH_2$, —$N(R_6)_2$, —$NHCOR_6$, —COOH, or —$COOR_6$ group wherein $R_6$ is lower alkyl;

Y is hydrogen, alkyl of 1 to 4 carbon atoms, halo or lower alkoxy; and

Z is —$OR_7$ or —$NR_7R_8$ wherein $R_7$ and $R_8$ are independently hydrogen or lower alkyl;

or a pharmaceutically acceptable salt thereof.

18. A method for inhibiting 3',5'-cyclic AMP phosphodiesterase which method comprises administering a cyclic AMP phosphodiesterase inhibiting amount of a compound of the formula

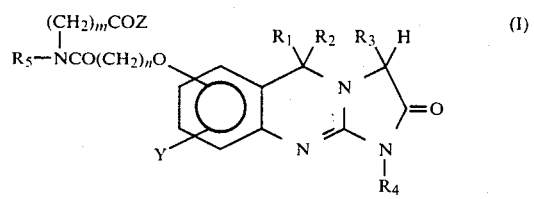

, its optical isomers, or a pharmaceutically acceptable salt thereof wherein:

m and n are integers of 1 to 6;

$R_1$ is hydrogen or alkyl of 1 to 4 carbons;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbons, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —$OCOR_6$, halo, L—$NH_2$, —$N(R_6)_2$, —$NHCOR_6$, —COOH, or —$COO(R_6)$ group wherein $R_6$ is lower alkyl; phenyl or phenyl lower alkyl wherein phenyl is unsubstituted or substituted with 1 or more lower alkyl, halo or lower alkoxy group or an —$NH_2$, —$N(R_6)_2$, —$NHCOR_6$, —COOH, or —$COOR_6$ group wherein $R_6$ is lower alkyl;

Y is hydrogen, alkyl of 1 to 4 carbon atoms, halo or lower alkoxy; and

Z is —$OR_7$ or —$NR_7R_8$ wherein $R_7$ and $R_8$ are independently hydrogen or lower alkyl.

19. The method according to claim 18 wherein the inhibition of said phosphodiesterase activity results in antithrombotic activity.

20. A method for treating heart failure which method comprises administering to a subject in need of such treatment a therapeutically effective amount of a compound of the formula

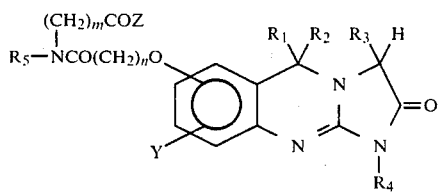

(I)

, its optical isomers, or a pharmaceutically acceptable salt thereof wherein:

m and n are integers of 1 to 6;

$R_1$ is hydrogen or alkyl of 1 to 4 carbon;

$R_2$ is hydrogen or $R_1$ and $R_2$ are combined to form an oxo group;

$R_3$ is hydrogen, alkyl of 1 to 6 carbon atoms, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbons, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_6$, halo, —NH$_2$, —N(R$_6$)$_2$, —NHCOR$_6$, —COOH, or —COO(R$_6$) group wherein R$_6$ is lower alkyl, phenyl or phenyl lower alkyl wherein phenyl is unsubstituted or substituted with 1 or more lower alkyl, halo or lower alkoxy groups or an —NH$_2$, —N(R$_6$)$_2$, —NHCOR$_6$, —COOH or —COOR$_6$ group wherein R$_6$ is lower alkyl;

Y is hydrogen, alkyl of 1 to 4 carbon atoms, halo or lower alkoxy; and

Z is —OR$_7$ or —NR$_7$R$_8$ wherein R$_7$ and R$_8$ are independently hydrogen or lower alkyl.

21. A method for treating spontaneous malignant tumor cell metastases mediated by platelets which method comprises administering to a subject (in need of such treatment a therapeutically effective amount of a compound of the formula

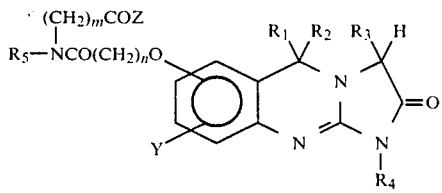

(I)

, its optical isomers, or a pharmaceutically acceptable salt thereof wherein:

m and n are integers of 1 to 6;

$R_1$ is hydrogen or alkyl of 1 to 4 carbon;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl and its aliphatic acylates of 1 to 6 carbon atoms or aryl acylates of 7 to 12 carbon atoms, carbamoyl alkyl, carboxyalkyl, alkoxycarbonylalkyl or α-amino acid side chains;

$R_4$ is hydrogen, alkyl of 1 to 6 carbons, benzyl, or hydroxy lower alkyl;

$R_5$ is hydrogen, alkyl of 1 to 6 carbon atoms, cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_6$, halo, —NH$_2$, —N(R$_6$)$_2$, —NHCOR$_6$, —COOH, or —COO(R$_6$) group wherein R$_6$ is lower alkyl; phenyl or phenyl lower alkyl wherein phenyl is unsubstituted or substituted with 1 or more lower alkyl, halo or lower alkoxy groups or an —NH$_2$, —N(R$_6$)$_2$, —NHCOR$_6$, —COOH, or —COOR$_6$ group wherein R$_6$ is lower alkyl;

Y is hydrogen, alkyl of 1 to 4 carbon atoms, halo or lower alkoxy; and

Z is —OR$_7$ or —NR$_7$R$_8$ wherein R$_7$ and R$_8$ are independently hydrogen or lower alkyl.

* * * * *